(12) United States Patent
Braganca et al.

(10) Patent No.: US 11,579,217 B2
(45) Date of Patent: Feb. 14, 2023

(54) DEVICES AND METHODS FOR FREQUENCY- AND PHASE-BASED DETECTION OF MAGNETICALLY-LABELED MOLECULES USING SPIN TORQUE OSCILLATOR (STO) SENSORS

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 436 days.

(21) Appl. No.: 16/819,636

(22) Filed: Mar. 16, 2020

(65) Prior Publication Data

US 2020/0326392 A1 Oct. 15, 2020

Related U.S. Application Data

(60) Provisional application No. 62/833,167, filed on Apr. 12, 2019.

(51) Int. Cl.
*G01R 33/09* (2006.01)
*G01R 33/12* (2006.01)
(Continued)

(52) U.S. Cl.
CPC ....... *G01R 33/1284* (2013.01); *G01N 27/745* (2013.01); *G01N 33/54313* (2013.01); *G01N 33/58* (2013.01)

(58) Field of Classification Search
CPC ........ G01R 33/09; G01R 33/12; G01R 33/44; G01N 27/327; G01N 27/72
See application file for complete search history.

(56) References Cited

U.S. PATENT DOCUMENTS 5,302,509 A 4/1994 Cheeseman
6,037,167 A 3/2000 Adelman et al.
(Continued)

FOREIGN PATENT DOCUMENTS

CN 102928596 A 2/2013
CN 103885000 A 6/2014
(Continued)

OTHER PUBLICATIONS

E. du Trémolet de Lacheisserie, D. Gignoux, and M. Schlenker (editors), Magnetism: Materials and Applications, vol. 2. Springer, 2005.
(Continued)

*Primary Examiner* — Neel D Shah

(57) ABSTRACT

Devices and methods for molecule detection using such devices are disclosed herein. A molecule detection device comprises at least one fluidic channel configured to receive molecules to be detected, a sensor comprising a spin torque oscillator (STO) and encapsulated by a material separating the sensor from the at least one fluidic channel, and detection circuitry coupled to the sensor. At least some of the molecules to be detected are labeled by magnetic nanoparticles (HNPs). A surface of the material provides binding sites for the molecules to be detected. The detection circuitry is configured to detect a frequency or frequency noise of a radio-frequency (RF) signal generated by the STO in response to presence or absence of at least one MNP coupled to one or more binding sites associated with the sensor.

34 Claims, 18 Drawing Sheets

(51) Int. Cl.
*G01R 33/44* (2006.01)
*G01N 27/327* (2006.01)
*G01N 27/72* (2006.01)
*G01N 27/74* (2006.01)
*G01N 33/58* (2006.01)
*G01N 33/543* (2006.01)

(56) References Cited

U.S. PATENT DOCUMENTS

| | | |
|---|---|---|
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |
| 8,432,644 B2 | 4/2013 | Braganca et al. |
| 8,462,461 B2 | 6/2013 | Braganca et al. |
| 8,513,029 B2 | 8/2013 | Zhou |
| 8,553,346 B2 | 10/2013 | Braganca et al. |
| 8,570,677 B2 | 10/2013 | Braganca et al. |
| 8,597,881 B2 | 12/2013 | Milton et al. |
| 8,652,810 B2 | 2/2014 | Adessi et al. |
| 8,654,465 B2 | 2/2014 | Braganca et al. |
| 8,675,309 B2 | 3/2014 | Braganca et al. |
| 8,728,729 B2 | 5/2014 | Bridgham et al. |
| 8,728,825 B2 | 5/2014 | Wang et al. |
| 9,121,062 B2 | 9/2015 | Balasubramanian et al. |
| 9,273,354 B2 | 3/2016 | Bridgham et al. |
| 9,297,006 B2 | 3/2016 | Adessi et al. |
| 9,435,791 B2 | 9/2016 | Acosta et al. |
| 9,453,258 B2 | 9/2016 | Kain et al. |
| 9,464,107 B2 | 10/2016 | Wegener et al. |
| 9,587,275 B2 | 3/2017 | Emig et al. |
| 9,605,310 B2 | 3/2017 | Balasubramanian et al. |
| 9,640,748 B2 | 5/2017 | Gotsmann et al. |
| 10,203,379 B2 | 2/2019 | Wang et al. |
| 10,260,095 B2 | 4/2019 | Esfandyarpour et al. |
| 10,591,440 B2 | 3/2020 | Astier et al. |
| 2004/0043479 A1 | 3/2004 | Briscoe et al. |
| 2004/0219695 A1 | 11/2004 | Fox |
| 2005/0054081 A1 | 3/2005 | Hassard et al. |
| 2005/0118102 A1 | 6/2005 | Xiang et al. |
| 2007/0224700 A1 | 9/2007 | Masters |
| 2007/0264159 A1 | 11/2007 | Graham et al. |
| 2008/0218165 A1 | 9/2008 | Kahlman et al. |
| 2008/0241569 A1 | 10/2008 | Qin et al. |
| 2009/0066318 A1 | 3/2009 | Kahlman et al. |
| 2009/0148857 A1 | 6/2009 | Srivastava et al. |
| 2009/0206832 A1 | 8/2009 | Kahlman et al. |
| 2009/0208957 A1 | 8/2009 | Korlach et al. |
| 2010/0039105 A1* | 2/2010 | Ryan ............ G01N 27/745 324/226 |
| 2010/0111768 A1 | 5/2010 | Banerjee et al. |
| 2010/0194386 A1 | 8/2010 | Prins et al. |
| 2010/0207631 A1 | 8/2010 | McDowell |
| 2010/0231214 A1 | 9/2010 | Zhou |
| 2011/0223612 A1 | 9/2011 | Wang et al. |
| 2012/0295262 A1 | 11/2012 | Ronaghi et al. |
| 2013/0148223 A1 | 6/2013 | Braganca et al. |
| 2014/0008281 A1 | 1/2014 | Ramanathan et al. |
| 2014/0139214 A1 | 5/2014 | Park et al. |
| 2014/0292318 A1 | 10/2014 | Wang et al. |
| 2016/0131613 A1 | 5/2016 | Jayant et al. |
| 2017/0304825 A1 | 10/2017 | Issadore et al. |
| 2018/0128822 A1 | 5/2018 | Wang et al. |
| 2018/0237850 A1* | 8/2018 | Mandell ............ B01L 3/502761 |
| 2018/0284200 A1 | 10/2018 | Chen et al. |
| 2019/0032114 A1 | 1/2019 | Trivedi |
| 2019/0170680 A1 | 6/2019 | Sikora et al. |
| 2019/0390267 A1 | 12/2019 | Astier et al. |
| 2021/0047681 A1 | 2/2021 | Mendonsa et al. |
| 2021/0047682 A1 | 2/2021 | Mendonsa et al. |

FOREIGN PATENT DOCUMENTS

| | | |
|---|---|---|
| EP | 1544310 A2 | 6/2005 |
| EP | 3208627 A1 | 8/2017 |
| ES | 2674264 | 6/2018 |
| WO | 2005047864 A3 | 9/2005 |
| WO | 2005124345 A2 | 12/2005 |
| WO | 2015031691 A1 | 3/2015 |
| WO | 2016183218 A1 | 11/2016 |
| WO | 2017030999 A1 | 2/2017 |
| WO | 2017061129 A1 | 4/2017 |
| WO | 2018017884 A1 | 1/2018 |
| WO | 2018186539 A1 | 10/2018 |
| WO | 2019068204 A1 | 4/2019 |
| WO | 2020210370 A1 | 10/2020 |

OTHER PUBLICATIONS

E. Hall, "On a New Action of the Magnet on Electric Currents," American Journal of Mathematics, vol. 2, 287, 1879.

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

International Search Report and Written Opinion from PCT Application No. PCT/US2020!027290 (filed Apr. 8, 2020), dated Jun. 25, 2020.

International Search Report and Written Opinion from PCT Application No. PCT/US2019/068131 (filed Dec. 20, 2019), dated Apr. 1, 2020.

International Search Report and Written Opinion from PCT Application No. PCT/US2019/068535 (filed Dec. 26, 2019), dated Apr. 26, 2020.

International Search Report and Written Opinion from PCT Application No. PCT/US2020/014707 (filed Jan. 23, 2020), dated May 11, 2020.

International Search Report and Written Opinion from PCT Application No. PCT/US2020/021776 (filed Mar. 9, 2020), dated Sep. 1, 2020.

International Search Report and Written Opinion from PCT Application No. PCT/US2020/023069 (filed Mar. 17, 2020), dated Jul. 20, 2020.

International Search Report and Written Opinion from PCT Application No. PCT/US2020/023078 (filed Mar. 17, 2020), dated Jul. 19, 2020.

International Search Report and Written Opinion from PCT Application No. PCT/US2020/035915 (filed Jun. 3, 2020), dated Aug. 26, 2020.

J. C. Slonczewski, "Current-driven excitation of magnetic multilayers," Journal of Magnetism and Magnetic Materials, vol. 159, L1, 1996.

(56) References Cited

OTHER PUBLICATIONS

L. Berger, "Emission of spin waves by a magnetic multilayer traversed by a current," Physical Review B, vol. 54, 9353, 1996.
Lany, M., G. Boero, and R. S. Popovic. "Superparamagnetic microbead inductive detector". Review of scientific instruments 76.8 (2005): 084301.
Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.
M. Díaz-Michelena, "Small Magnetic Sensors for Space Applications," Sensors, vol. 9, 2271, 2009.
Michael L. Metzker, "Sequencing Technologies—the Next Generation," Nature Rev. Genet. 11: 31-46 (2009).
Miller, M. M., et al. "A DNA array sensor utilizing magnetic microbeads and magnetoelectronic detection". Journal of Magnetism and Magnetic Materials 225.1-2 (2001): 138-144.
P. Anderson, J. Rowell, "Probable Observation of the Josephson Superconducting Tunneling Effect," Physical Review Letters, vol. 10, 230, 1963.
P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.
P. Namdari, H. Daraee, and A. Eatemadi, "Recent Advances in Silicon Nanowire Biosensors: Synthesis Methods, Properties and Applications", Nanoscale Research Letters, vol. 11, 406, 2016.
Quynh, L. K., et al. Detection of magnetic nanoparticles using simple AMR sensors in Wheatstone bridge. Journal of Science: Advanced Materials and Devices, 2016, 1.1: 98-102.
R. C. Jaklevic, J. Lambe, A. H. Silver & J. E. Mercereau, "Quantum Interference Effects in Josephson Tunneling," Physical Review Letters, vol. 12, 159, 1964.
R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions on Magnetics, vol. 48, 1758, 2012.
Rabehi, A., Electromagnetic microsystem for the detection of magnetic nanoparticles in a microfluidic structure for mmunoassays (Doctoral dissertation). Jan. 29, 2020.
Rauwerdink, A. M., Giustini, A. J., & Weaver, J. B. (2010). Simultaneous quantification of multiple magnetic nanoparticles. Nanotechnology, 21(45), 455101.
Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.
Srimani T. et al., "High Sensitivity Biosensor using Injection Locked Spin Torque Nano-Oscillators," arXiv:1511.09072, Nov. 2015.
Tang, C., He, Z., Liu, H., Xu, Y., Huang, H., Yang, G., . . . & Chen, Z. (2020). Application of magnetic nanoparticles in nucleic acid detection Journal of Nanobiotechnology, 18, 1-19. Apr. 21, 2020.
Wang, W., & Jiang, Z., "Thermally assisted magnetic tunneling junction for biosensing applications," IEEE Transactions on Magnetics, 43(6), 2406-2408, Jun. 30, 2007.
Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).
Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.
Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.

Ye, F., Zhao, Y., El-Sayed, R., Muhammed, M., & Hassan, M. (2018). Advances in nanotechnology for cancer biomarkers. Nano Today, 18, 103-123.
Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.
Daschiel et al. The holy grail of microfluidics: sub-laminar drag by layout of periodically embedded microgrooves (2013) MicrofluidNanofluid 15, 675-687.
Mao et al. A Microfluidic Device with a Linear Temperature Gradient for Parallel and Combinatorial Measurements (2002) J AmChem Soc 124, 4432-4435.
Qiu et al. Instrument-free point-of-care molecular diagnosis of H 1 N 1 based on microfluidic convective PCR (2017) Sensors andActuators B: Chemical 243, 738-744.
U.S. Appl. No. 62/833,130, filed Apr. 12, 2019, Yann Astier, Entire Document.
A. Seki, et al., "Study of the heating characteristics and mechanisms of magnetic nanoparticles over a wide range of frequencies and amplitudes of an alternating magnetic field," Journal of Physics: Conference Series 521 (2014).
A.M. Sydor et al., "Super-Resolution Microscopy: From Single Molecules to Supramolecular Assemblies," Trends in Cell Biology, Dec. 2015, vol. 25, No. 12, pp. 730-748.
B. N. Engel, et al., "A4-Mb Toggle MRAM Based on a Novel Bit and Switching Method," IEEE Transactions on Magnetics, vol. 41, No. 1, Jan. 2005.
C. Chappert et al., "The emergence of spin electronics in data storage," Nature Materials, Dec. 2007.
C.H. Smith et al., "High-resolution giant magnetoresistance on-chip arrays for magnetic imaging," Journal of Applied Physics 93, 6864 (2003).
D. Ross et al., "Temperature Measurement in Microfluidic Systems Using a Temperature-Dependent Fluorescent Dye," Anal. Chem. 2001, 73, 17, 4117-4123, Jul. 24, 2001.
EPHOTOzine.com, "Complete Guide to Image Sensor Pixel Size," Aug. 2, 2016, available at https://www.ephotozine.com/article/complete-guide-to-image-sensor-pixel-size-29652.
F. Grasset et al., "Synthesis, magnetic properties, surface modification and cytotoxicity evaluation of Y3Fe5—xAlxO12 (0?x?2) garnet submicron particles for biomedical applications," Journal of Magnetism and Magnetic Materials, vol. 234, Issue 3, Sep. 2001, pp. 409-418.
F. Menges et al., "Temperature mapping of operating nanoscale devices by scanning probe thermometry," Nature Communications, 7:10874, Mar. 3, 2016.
Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).
Illumina, "NovaSeq 6000 Sequencing System," 2019, available at https://www.illumina.com/systems/sequencing-platforms/novaseq.html.
International Search Report from PCT App. No. PCT/US2016/046888, dated Oct. 26, 2016.
J. Sakakibara et al., "Measurements of thermally stratified pipe flow using image-processing techniques," Experiments in Fluids, Dec. 1993, vol. 16, Issue 2, pp. 82-96.
John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 /011007-1.
Lin Gui and Carolyn L. Ren, "Temperature measurement in microfluidic chips using photobleaching of a fluorescent thin film," Applied Physics Letters 92, 024102, 2008.
M. Aslam et al., "Silica encapsulation and magnetic properties of FePt nanoparticles," Journal of Colloid and Interface Science 290 (2005) 444-449.
M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.

(56) References Cited

OTHER PUBLICATIONS

M.T. Tlili et al., "Magnetic, Electrical Properties and Spin-Glass Effect of Substitution of Ca for Pr in Ca2—xPrxMnO4 Compounds," The Open Surface Science Journal, 2009, vol. 1, pp. 54-58.

N. X. Phuc, et al., "Tuning of the Curie Temperature in La1—xSrxMn1—yTiyO3" J. Korean Phy. Soc., vol. 52, No. 5, May 2008, pp. 1492-1495.

N.R. Patil et al., "Effect of temperature on the fluorescence emission of ENCTTTC in different nonpolar solvents," Can. J. Phys. 91: 971-975 (2013).

R. Giri, "Temperature effect study upon the fluorescence emission of substituted coumarins," Spectrochimica Acta Part A: Molecular Spectroscopy, vol. 48, Issue 6, Jun. 1992, p. 843-848.

S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.

S.I. Kiselev et al., "Microwave oscillations of a nanomagnet driven by a spin-polarized current," Nature 425, pp. 380-383, 2003.

T. Nagasawa et al., "Delay detection of frequency modulation signal from a spin-torque oscillator under a nanosecond-pulsed magnetic field," Journal of Applied Physics, vol. 111, 07C908 (2012).

W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.

Weifeng Shen et al., "Detection of DNA labeled with magnetic nanoparticles using MgO-based magnetic tunnel function sensors," Journal of Applied Physics 103, 07A306 (2008).

International Search Report and Written Opinion from PCT Application No. PCT/US2021/021274 (filed Mar. 7, 2021), dated Sep. 28, 2021.

International Search Report and Written Opinion from PCT Application No. PCT/US2021/028263 (filed Apr. 21, 2021), dated Aug. 26, 2021.

International Search Report and Written Opinion from PCT Application No. PCT/US2021/040767 (filed Jul. 8, 2021), dated Oct. 25, 2021.

* cited by examiner

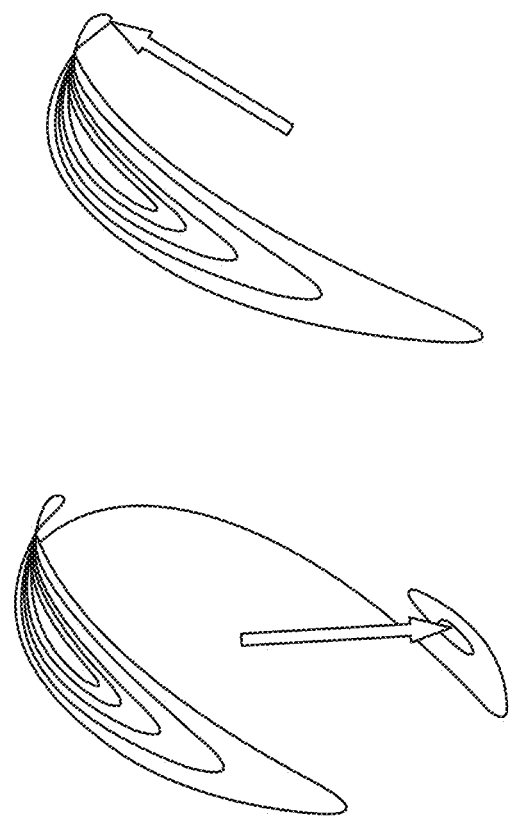
FIG. 3C
FIG. 3B
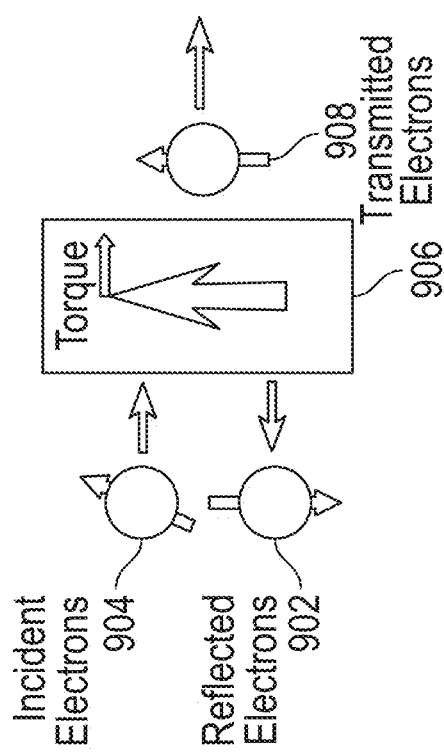
FIG. 3A

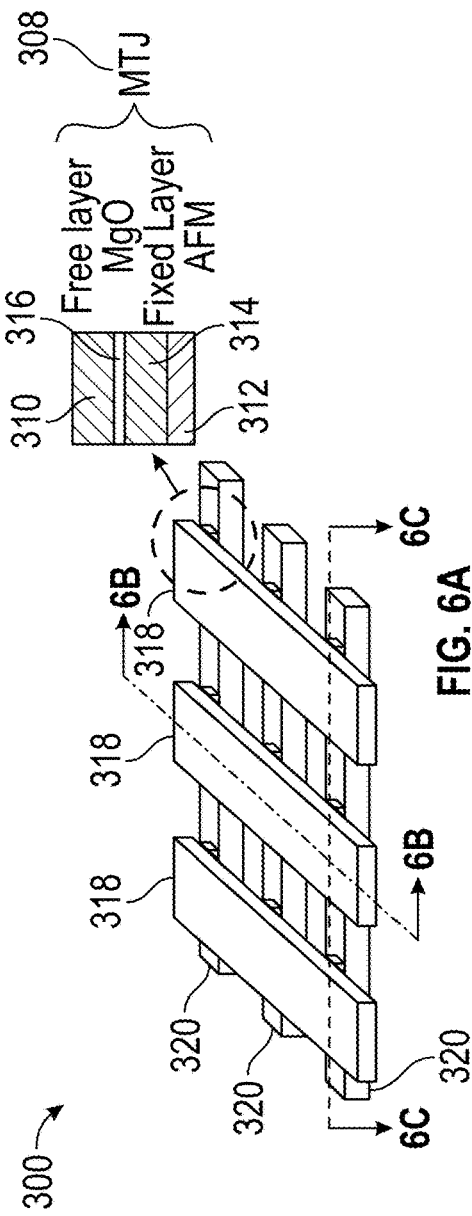
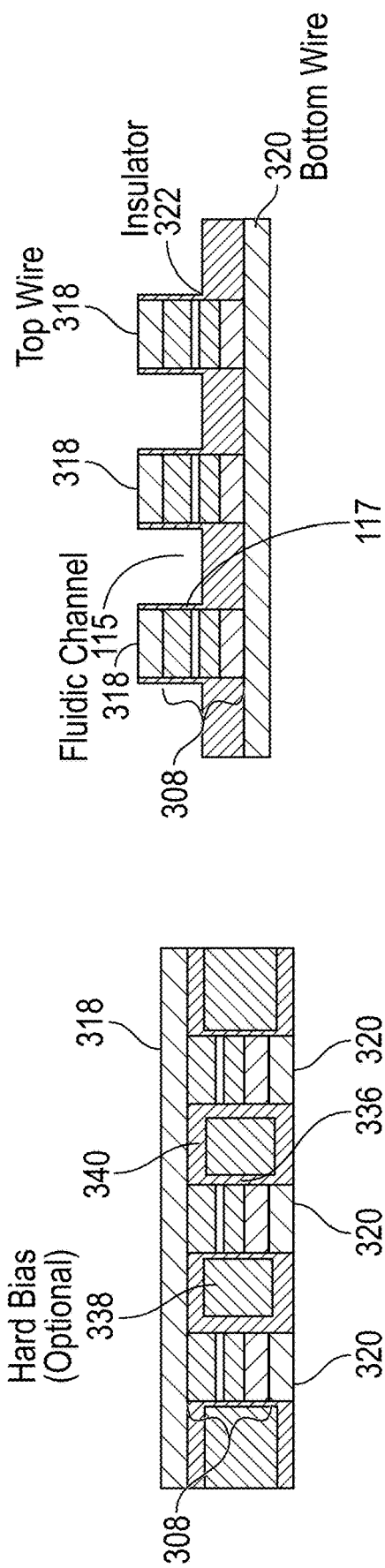

DEVICES AND METHODS FOR FREQUENCY- AND PHASE-BASED DETECTION OF MAGNETICALLY-LABELED MOLECULES USING SPIN TORQUE OSCILLATOR (STO) SENSORS

CROSS-REFERENCE TO RELATED APPLICATIONS

This application claims the benefit of and hereby incorporates by reference, for all purposes, the entirety of the contents of U.S. Provisional Application No. 62/833,167, filed Apr. 12, 2019 and entitled "SPIN TORQUE OSCILLATOR (STO) SENSORS USED IN NUCLEIC ACID SEQUENCING ARRAYS AND DETECTION SCHEMES FOR NUCLEIC ACID SEQUENCING INCLUDING FREQUENCY- AND PHASE-BASED DETECTION SCHEMES." This application also incorporates by reference, for all purposes, the entirety of U.S. application Ser. No. 16/791,759, filed Feb. 14, 2020 and entitled "SPIN TORQUE OSCILLATOR (STO) SENSORS USED IN NUCLEIC ACID SEQUENCING ARRAYS AND DETECTION SCHEMES FOR NUCLEIC ACID SEQUENCING."

BACKGROUND

Field of the Disclosure

Embodiments of the present disclosure generally relate to magnetoresistive (MR) sensor arrays for detection of molecules coupled to magnetic nanoparticles (MNPs), such as for nucleic acid sequencing such as deoxyribonucleic acid (DNA) sequencing, and methods of using such MR sensor arrays for molecule detection.

Description of the Related Art

Current state-of-the-art sequencing systems are based on fluorescence signal detection and provide throughputs of 20 billion reads per run (https://www.illumina.com/systems/sequencing-platforms/novaseq.html). Achieving such performance, however, can require large-area flow cells, high-precision free-space imaging optics, and expensive high-power lasers to generate sufficient fluorescence signals for successful base detection.

One type of nucleic acid sequencing used for DNA sequencing is known as "sequencing by synthesis" (SBS). SBS involves binding of primer-hybridized template DNA, incorporation of a deoxynucleoside triphosphate (dNTP), and detection of incorporated dNTP. Gradual increases in SBS throughput have been accomplished in two ways, the first being an outward scaling, where the size and the number of flow cells in the sequencers is increased. This approach increases both the cost of reagents and the price of the sequencing system, as more high-power lasers and high-precision nano-positioners must be employed. The second approach involves inward scaling, where the density of DNA testing sites is increased so that the total number of sequenced DNA strands in a fixed-size flow cell is higher. To accomplish inward scaling, increasingly higher numerical aperture (NA) lenses must be employed to distinguish the signal from neighboring fluorophores as the spacing between them decreases. However, this approach cannot be implemented indefinitely, as the Rayleigh criterion puts the distance between resolvable light point sources at $0.61\lambda/NA$, constraining the minimum distance between two sequenced DNA strands to be no smaller than approximately 400 nm. Similar resolution limits apply to sequencing directly on top of imaging arrays (similar to cell phone cameras), where the smallest pixel size achieved so far is approximately 1 μm (https://www.ephotozine.com/article/complete-guide-to-image-sensor-pixel-size -29652).

The Rayleigh criterion currently represents the fundamental limitation for inward scaling of optical SBS systems, which can only be overcome by applying super-resolution imaging techniques (see A. M. Sydor, K. J. Czymmek, E. M. Puchner, and V. Mannella, "Super-Resolution Microscopy: From Single Molecules to Supramolecular Assemblies," Special Issue: Quantitative Cell Biology, Vol. 25, 730, 2015) and has not yet been achieved in highly multiplexed systems. Hence, increasing throughput and decreasing cost of optical SBS sequencers has been slow due to the need to build bigger flow cells and implement more expensive optical scanning and imaging systems.

Therefore, there is a need for new and improved apparatuses for and methods of detecting the presence of molecules such as nucleic acids that overcome the limitations of conventional apparatuses and methods.

SUMMARY

This summary represents non-limiting embodiments of the disclosure.

Disclosed herein are improved detection devices, systems, and methods that use magnetic nanoparticles (MNPs) to allow molecules (e.g., nucleic acids) to be identified. The disclosures herein include embodiments having sensors with spin torque oscillators (STO) that allow for detection of characteristics indicating the presence or absence of MNPs near sensors. Also disclosed herein are detection methods that can be used to detect (e.g., measure or obtain) characteristics or changes in characteristics of radio-frequency (RF) signals generated by the sensors, where the detected characteristics or changes in characteristics are indicative of the presence or absence of MNPs (e.g., in response to a magnetic field generated, or not generated, by a magnetic nanoparticle label).

In some embodiments, a device for molecule detection comprises at least one fluidic channel configured to receive molecules to be detected, wherein at least some of the molecules to be detected are labeled by MNPs, a sensor comprising a STO and encapsulated by a material separating the sensor from the at least one fluidic channel, wherein a surface of the material provides binding sites for the molecules to be detected, and detection circuitry coupled to the sensor and configured to detect a frequency or frequency noise of a RF signal generated by the STO in response to presence or absence of at least one MNP coupled to one or more binding sites associated with the sensor.

In some embodiments, the detection circuitry is configured to detect the frequency or the frequency noise of the RF signal generated by the STO in response to the presence or absence of the at least one MNP coupled to the one or more binding sites associated with the sensor by, in part, applying a DC current to the STO.

In some embodiments, the molecules to be detected include a first type of molecule and a second type of molecule, the first type of molecule being labeled by a first MNP type, and the second type of molecule being labeled by a second MNP type, the frequency or frequency noise of the RF signal generated by the STO is (a) a first frequency or frequency noise in response to presence of the first MNP type, or (b) a second frequency or frequency noise in response to presence of the second MNP type, and the detection circuitry is configured to distinguish between the first frequency or frequency noise and the second frequency or frequency noise to differentiate between the first and second types of molecules.

In some embodiments, the detection circuitry comprises a delay line circuit. If present, the delay line circuit may comprise a power divider configured to split the signal generated by the STO, or an amplified version of the signal generated by the STO, into a first signal routed to a first path (e.g., a first wire trace) having a first delay and a second signal routed to a second path (e.g., a second wire trace) having a second delay, wherein the second delay is greater than the first delay (e.g., if the first and second paths are wire traces, the second wire trace is longer than the first), a mixer having a first input coupled to the first path, a second input coupled to the second path, and an output, and a low pass or band pass filter coupled to the output of the mixer.

In embodiments that include a delay line circuit, the delay line circuit may also include (a) a first amplifier coupled to the power divider and disposed between the STO and the power divider to provide the amplified version of the signal generated by the STO to the power divider, and/or (b) a second amplifier coupled to an output of the low pass or band pass filter.

In embodiments that include a delay line circuit, the delay line circuit may also include a phase shifter disposed on either the first or second path between the power divider and the mixer. If present, the phase shifter is configured to adjust a difference between a phase of the first signal and a phase of the second signal so that, in the absence of the at least one MNP coupled to one or more binding sites associated with the sensor, a DC output of the line delay circuit is below a threshold.

In some embodiments, the device further comprises a spectrum analyzer coupled to an output of the low pass or band pass filter. If present, the spectrum analyzer may be implemented via non-transitory machine-executable instructions for execution by a processor.

In some embodiments, a system comprises a device for molecule detection that includes detection circuitry having a delay line circuit and a spectrum analyzer coupled to an output of the device's detection circuitry.

In some embodiments including a delay line circuit, the MNPs used are superparamagnetic, and the delay line circuit comprises a spectrum analyzer configured to detect the frequency noise of the RF signal generated by the STO based on a comparison of a measured integrated noise from the STO to a noise measurement from a reference STO not exposed to any MNP. If present, the spectrum analyzer may be implemented by a processor.

In some embodiments, the detection circuitry comprises a phase locked loop (PLL) configured to provide an error signal output that corresponds to the frequency noise of the RF signal generated by the STO in response to the presence of the at least one MNP coupled to the one or more binding sites associated with the sensor. In embodiments in which the detection circuitry comprises a PLL, the PLL may comprise a loop filter, and a low pass filter. If present, the loop filter may comprise an amplifier and at least one resistor.

In some embodiments in which the detection circuitry comprises a PLL, the detection circuitry further comprises a mixer having a first input, a second input, and an output, and a reference oscillator with an input coupled to a tuning input from the PLL and an output coupled to the first input of the mixer. In some such embodiments, the STO is coupled to the second input of the mixer, and the output of the mixer is coupled to an input of the low pass filter.

In some embodiments, the STO comprises a pinned layer, a free layer, and a spacer layer disposed between the pinned layer and the free layer. The pinned layer may comprise one or more ferromagnetic (FM) layers. In some embodiments, the one or more FM layers are first one or more FM layers, and the free layer comprises second one or more FM layers. The spacer layer may comprise an insulating layer or a metal layer. In some embodiments, in a quiescent state of magnetization (when the STO is not oscillating), a magnetic moment of the free layer is oriented substantially co-linearly with a magnetic moment of the pinned layer. In some embodiments, in a quiescent state of magnetization, a magnetic moment of the free layer is oriented substantially parallel to or anti-parallel to a magnetic moment of the pinned layer. In some embodiments, in a quiescent state of magnetization, a magnetic moment of the free layer is oriented at an angle to a magnetic moment of the pinned layer, wherein the angle is between approximately 20 degrees and approximately 60 degrees.

Also disclosed herein is a method of sequencing nucleic acid using a device, the device comprising a plurality of STOs and at least one fluidic channel, the method comprising labeling a nucleotide precursor with a MNP, adding the labeled nucleotide precursor to the at least one fluidic channel of the device, detecting a frequency or frequency noise of a RF signal generated by at least one of the plurality of STOs, and, based at least in part on the detected frequency or frequency noise of the RF signal generated by the at least one of the plurality of STOs, determining whether the labeled nucleotide precursor has been detected.

In some embodiments, detecting the frequency or frequency noise of the RF signal generated by at least one of the plurality of STOs comprises detecting an amplitude of a DC signal at an output of a delay line circuit coupled to the at least one of the plurality of STOs. In some embodiments, detecting the frequency or frequency noise of the RF signal generated by at least one of the plurality of STOs comprises monitoring an error signal of a detection circuit comprising a phase locked loop.

In some embodiments, the MNP is superparamagnetic, and detecting the frequency or frequency noise of the RF signal generated by at least one of the plurality of STOs comprises determining a spectral density of the RF signal generated by the at least one of the plurality of STOs, integrating the spectral density, and comparing the integrated spectral density to a reference noise associated with a reference STO, the reference STO not being influenced by any MNP.

In some embodiments, the method further comprises binding at least one nucleic acid strand to a binding site in the fluidic channel before adding the labeled nucleotide precursor to the fluidic channel of the device, and adding, to the fluidic channel, an extendable primer and a plurality of molecules of nucleic acid polymerase.

In some embodiments, the method further comprises, in response to determining that the labeled nucleotide precursor has been detected, recording (a) an identity of the nucleotide precursor, or (b) an identity of a base complementary to the labeled nucleotide precursor.

Also disclosed herein is a method of sequencing nucleic acid using a device, the device comprising a plurality of STOs and at least one fluidic channel, the method comprising labeling a first nucleotide precursor with a first MNP type, the first MNP type selected to cause a magnetization of each of the plurality of STOs to oscillate at a first frequency, labeling a second nucleotide precursor with a second MNP type, the second MNP type selected to cause the magnetization of each of the plurality of STOs to oscillate at a second frequency, adding the labeled first and second nucleotide precursors to the fluidic channel of the device, using a delay line circuit, detecting a frequency of a signal generated by at least one of the plurality of STOs, and in response to the detected frequency, identifying whether the first nucleotide precursor or the second nucleotide precursor has been detected.

In some such embodiments, detecting the frequency of the signal generated by the at least one of the plurality of STOs comprises splitting a signal originating from the at least one of the plurality of STOs into a first signal and a second signal, routing the first signal to a mixer via a first path (e.g., a first wire trace) having a first delay, routing the second signal to the mixer via a second path (e.g., a second wire trace) having a second delay, the second delay being longer than the first delay, the mixer mixing the delayed first and second signals, and a low pass filter filtering an output from the mixer. In some such embodiments, identifying whether the first nucleotide precursor or the second nucleotide precursor has been detected comprises analyzing an output of the low pass filter or an amplified version of the output of the low pass filter. In some such embodiments, detecting the frequency of the signal generated by the at least one of the plurality of STOs further comprises shifting a phase of the first signal or the second signal. In some embodiments, detecting the frequency of the signal generated by the at least one of the plurality of STOs further comprises amplifying the output of the low pass filter.

In some embodiments, analyzing the output of the low pass filter or the amplified version of the output of the low pass filter comprises accessing a look-up table to determine whether the output of the low pass filter or the amplified version of the output of the low pass filter corresponds to a first expected value for the first nucleotide precursor or a second expected value for the second nucleotide precursor, or determining whether the output of the low pass filter or the amplified version of the output of the low pass filter is in a first range associated with the first nucleotide precursor or a second range associated with the second nucleotide precursor.

Also disclosed herein is a system for sequencing nucleic acid, the system comprising a plurality of STOs, at least one fluidic channel. means for labeling a nucleotide precursor with a MNP, means for adding the labeled nucleotide precursor to the at least one fluidic channel, means for detecting a frequency or frequency noise of a RF signal generated by at least one of the plurality of STOs, and means for determining, based at least in part on the detected frequency or frequency noise of the RF signal generated by the at least one of the plurality of STOs, whether the labeled nucleotide precursor has been detected.

In some embodiments, the system further comprises means for binding at least one nucleic acid strand to a binding site in the fluidic channel, and means for adding an extendable primer and a plurality of molecules of nucleic acid polymerase to the fluidic channel. The system may further comprise means for recording (a) an identity of the nucleotide precursor, (b) an identity of a base complementary to the labeled nucleotide precursor, or (c) both (a) and (b).

BRIEF DESCRIPTION OF THE DRAWINGS

So that the manner in which the above-recited features of the present disclosure can be understood in detail, a more particular description of the disclosure is in reference to embodiments, some of which are illustrated in the appended drawings. It is to be noted, however, that the appended drawings illustrate only typical embodiments of this disclosure and are therefore not to be considered limiting of its scope, for the disclosure may admit to other equally-effective embodiments.

FIGS. 3A, 3B, and 3C illustrate operating principles of STO-based sensors in accordance with some embodiments.

FIGS. 6A, 6B, and 6C illustrate a cross-point array architecture of sensor elements in accordance with some embodiments.

To facilitate understanding, identical reference numerals have been used, where possible, to designate identical elements that are common to the figures. It is contemplated that elements disclosed in one embodiment may be beneficially utilized in other embodiments without specific recitation.

DETAILED DESCRIPTION

Figure 1A:
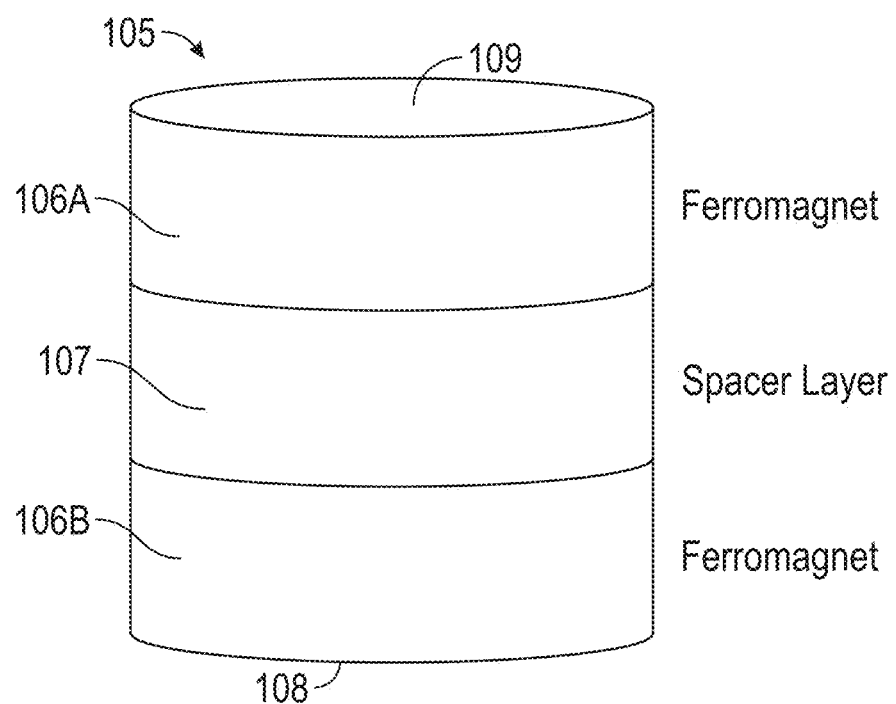
FIG. 1A illustrates a portion of a sensor in accordance with some embodiments.

Disclosed herein are improved detection devices, systems, and methods that use magnetic nanoparticles (MNPs)

to allow molecules (e.g., nucleic acids) to be identified. The disclosures herein include embodiments having sensors with spin torque oscillators (STO) that allow for detection of characteristics indicating the presence or absence of MNPs near sensors. Also disclosed herein are detection methods that can be used to detect (e.g., measure or obtain) characteristics or changes in characteristics of radio-frequency (RF) signals generated by the sensors, where the detected characteristics or changes in characteristics are indicative of the presence or absence of MNPs (e.g., in response to a magnetic field generated, or not generated, by a magnetic nanoparticle label). For example, devices and methods may determine whether a sensor is or is not generating a signal having a frequency at a particular frequency or within a specified range of frequencies, and, based thereon, determine whether one or more MNPs are being detected by the sensor. As another example, devices and methods may detect the frequency/phase noise of a signal generated by a sensor and, based thereon, determine whether one or more MNPs are being detected by the sensor and/or the type of MNP detected.

In some embodiments, MNPs are coupled to molecules to be detected. For example, in DNA sequencing applications, the MNPs may label nucleotide precursors that are then incorporated into a target DNA strand affixed to a binding site in the vicinity of a sensor. As a result of the incorporation of a MNP-labeled nucleotide precursor, at least one MNP is in the vicinity of the sensor, and its presence can have an impact on the behavior of the STO. This impact can be detected to detect the presence of the MNP. Presence of the MNP can then be used to determine that a particular nucleotide precursor has been incorporated into the target DNA strand.

As used herein, the term "spin torque oscillator" and acronym "STO" refer to any device that takes advantage of spin-torque-induced precession of magnetization caused by spin polarized currents.

The terms "frequency noise," "phase noise," and "frequency/phase noise" are used interchangeably herein. These terms are used to refer to random fluctuations of the instantaneous frequency of an oscillating signal.

In the following description, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in a claim (or in multiple claims). Likewise, reference to "the disclosure" shall not be construed as a generalization of any inventive subject matter disclosed herein and shall not be considered to be an element or limitation of the appended claims except where explicitly recited in a claim (or multiple claims).

It is to be understood at the outset that the disclosures herein may be used to detect any type of molecule to which a magnetic particle can be attached or coupled. The disclosure presumes that the particles attached to the molecules to be detected are magnetic nanoparticles, but this presumption is exemplary and is not intended to be limiting. Thus, the term "magnetic nanoparticle" and the acronym "MNP" include all types of magnetic particles that can be attached or coupled to molecules to be detected.

Accordingly, any molecule type that can be labeled by a magnetic nanoparticle may be detected using the devices and methods disclosed herein. Such molecule types may be biologic molecule types, such as proteins, antibodies, etc. For example, the disclosures herein may be used to detect nucleic acids (e.g., in DNA sequencing). The disclosures herein may also be used to detect non-biologic (inorganic or non-living) molecules, such as contaminants, minerals, chemical compounds, etc. The presentation of portions of the disclosure in the context of nucleic acid sequencing is solely exemplary and is not intended to limit the scope of the present disclosure. Accordingly, although some of the disclosure herein is provided in the context of nucleic acid sequencing, and specifically DNA sequencing, it is to be understood that the embodiments herein generally may be used to detect any type of molecule to which a magnetic nanoparticle can be attached.

Furthermore, although the description herein focuses on DNA as an exemplary nucleic acid, the various embodiments described can be applied to nucleic acid sequencing in general. Similarly, although SBS is used for illustrative purposes in the following description, the various embodiments are not so limited to SBS sequencing protocols (e.g., dynamic sequencing could be used instead).

Conventional nucleic acid sequencing, such as that used for DNA sequencing, typically relies on the detection of fluorescence. Specifically, fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, conventional fluorescent sequencing technologies utilize identifiably-distinct fluorescent moieties, each attached to one of the four nucleotides A, T, C, and G that are utilized in a sequencing reaction.

One conventional method of DNA sequencing involves adapting single-strand DNA (ssDNA) for attachment to a solid support of a sequencing apparatus and amplifying the quantity of the ssDNA using techniques such as the polymerase chain reaction to create many DNA molecules with a short leader. An oligo complementary to the short leader may then be added so that there is a short section of double-stranded DNA (dsDNA) at the leader. The double stranded portion of the bound molecule is a primer for a suitable DNA polymerase, such as, for example, Taq polymerase, which is operable at high temperatures.

The sequencing can then take one of several approaches. For example, the sequencing can use a mixture of four fluorescently-labeled 3'-blocked dNTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different fluorescent label), and the different labels are distinguishable by fluorescent spectroscopy or by other optical means.

Four fluorescently-labeled nucleotide precursors can be used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging. Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors (wavelengths). Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

As explained previously, the disclosures herein may be used to detect any type of molecule (e.g., biologic, organic, inorganic, or non-living) to which a magnetic particle (e.g., a MNP) can be attached. Apparatuses and methods disclosed herein use MNPs and sensors to perform detection of molecules, such as in nucleic acid sequencing (e.g., DNA sequencing using SBS chemistry methods). Specifically, embodiments of this disclosure include sensors comprising STOs that can be used to detect magnetic fields (or changes in magnetic fields) emitted by MNPs, and, specifically to distinguish between the presence and absence of magnetic fields emitted, or not emitted, by MNPs near the sensors. Embodiments that use the same MNP type for all molecules to be detected are disclosed, as are embodiments that use multiple MNP types, each type labeling a different molecule type. The disclosed embodiments allow different types of molecules to be distinguished.

Embodiments of the present disclosure also include various detection methods to obtain or determine (e.g., measure) characteristics of or outputs from the sensors (e.g., a change in oscillation frequency and/or frequency noise) caused by MNPs used as labels being near the sensors. Knowledge of which particular molecule type (e.g., in DNA sequencing applications, the type of nucleotide precursor) to which the particular MNP label has been attached may then be used to identify the particular molecule type (e.g., in DNA sequencing applications, the last-paired base of the ssDNA strand that is complementary to the identified nucleotide precursor).

STO Sensors

In some embodiments disclosed herein, a spin torque oscillation magnetoresistive sensor is provided to sense magnetic fields caused by MNPs coupled to molecules being detected. The sensor is configured to detect a precessional oscillation frequency or the noise in the precessional oscillation frequency of a magnetization of a magnetic layer to sense the magnetic field of a MNP. The sensor can include a magnetic free layer, a magnetic pinned layer, and a non-magnetic layer between the free and pinned layers. In operation, detection circuitry coupled to these layers induces an electrical (DC) current through the layers. Spin polarization of electrons traveling through the sensor causes a spin-torque-induced precession of the magnetization of one or more of the layers. The frequency of and/or noise in this oscillation changes in response to a magnetic field generated by a MNP in the vicinity of the sensor.

In some embodiments, knowledge of how the presences of a particular type of MNP is expected to change the frequency of oscillations of the sensor or noise in the oscillation frequency (frequency noise) can be used to detect the presence, or absence, of the magnetic field and, therefore, the MNP. In some embodiments, the expected effect of a particular type of MNP on the oscillation frequency of the sensor is known. For example, the presence of the particular type of MNP may cause the sensor to oscillate at a frequency f1, where f1 is different from the frequency f0 at which the sensor oscillates in the absence of the particular type of MNP, and the measured frequency can be used to detect the presence or absence of the particular type of MNP in the vicinity of the sensor. Specifically, if the measured oscillation frequency is f1, it can be deduced that there is at least one MNP in the vicinity of the sensor, and if the measured oscillation frequency is f0, it can be deduced that there is no MNP in the vicinity of the sensor. As another example, the particular type of MNP may induce noise in the oscillation frequency (referred to as phase noise or frequency noise), and the detection of the presence of or an increase in this noise can allow the presence of the MNP to be detected. Likewise, absence of frequency noise in the oscillations of the sensor, or frequency noise below a threshold, can be used to determine that the sensor is not being influenced by any MNPs.

FIG. 1A illustrates a tri-layer structure of a sensor 105 in accordance with some embodiments. The exemplary sensor 105 of FIG. 1 has a bottom 108 and a top 109. The sensor 105 comprises a STO, which is a patterned magnetic device with an active area including three layers, shown in FIG. 1A as two ferromagnetic (FM) layers 106A, 106B separated by a nonmagnetic spacer layer 107.

In some embodiments in which the STO is a thin-film device, the FM layers 106A, 106B are engineered to have their magnetic moments oriented either substantially in the plane of the film or substantially perpendicular to the plane of the film. Suitable materials for use in the FM layers 106A, 106B include, for example, alloys of Co, Ni, and Fe (sometimes mixed with other elements). The example materials described above are merely exemplary and are not intended to be limiting. Materials suitable for use in the FM layers 106A, 106B are known to those having ordinary skill in the art.

The nonmagnetic spacer layer 107 may be, for example, a metallic material or combination of metallic materials, such as, for example, copper or silver, in which case the structure is called a spin valve (SV). Alternatively, the nonmagnetic spacer layer 107 may be an insulator material such as, for example, alumina (also known in the art as aluminum oxide) or magnesium oxide, in which case the structure is referred to as a magnetic tunnel junction (MTJ). The materials identified for the insulator material are merely exemplary and are not intended to be limiting. Materials suitable for use in the nonmagnetic layer 107 are known to those having ordinary skill in the art.

The active region of the sensor 105 lies in the tri-layer structure shown in FIG. 1A. As described further below in the discussion of FIG. 1B, additional layers may be added above and below the layers 106A, 106B, 107 shown in FIG. 1A to serve various purposes, such as, for example, interface smoothing, texturing, and protection from processing used to pattern the overall detection device (e.g., as shown and described below in the context of, e.g., FIGS. 4A-4C, 5A-5D, etc.) and passivation/protection of the sensor 105. Accordingly, a component that is in contact with a magnetic sensor 105 may be in contact with one of the three illustrated layers 106A, 106B, or 107, or it may be in contact with another part of the sensor 105 that is not illustrated in FIG. 1A.

As described further below, the magnetic moment of one or both FM layers 106A, 106B of the sensor 105 can be excited into precessional orbits by applying an electric current to the device through an effect known as spin transfer. Spin transfer (sometimes referred to as spin torque transfer) involves the interaction of a spin polarized current (i.e., a current that has some large fraction of electrons with spins oriented in the same direction) with a FM layer (e.g., layer 106A or 106B).

Figure 1B:
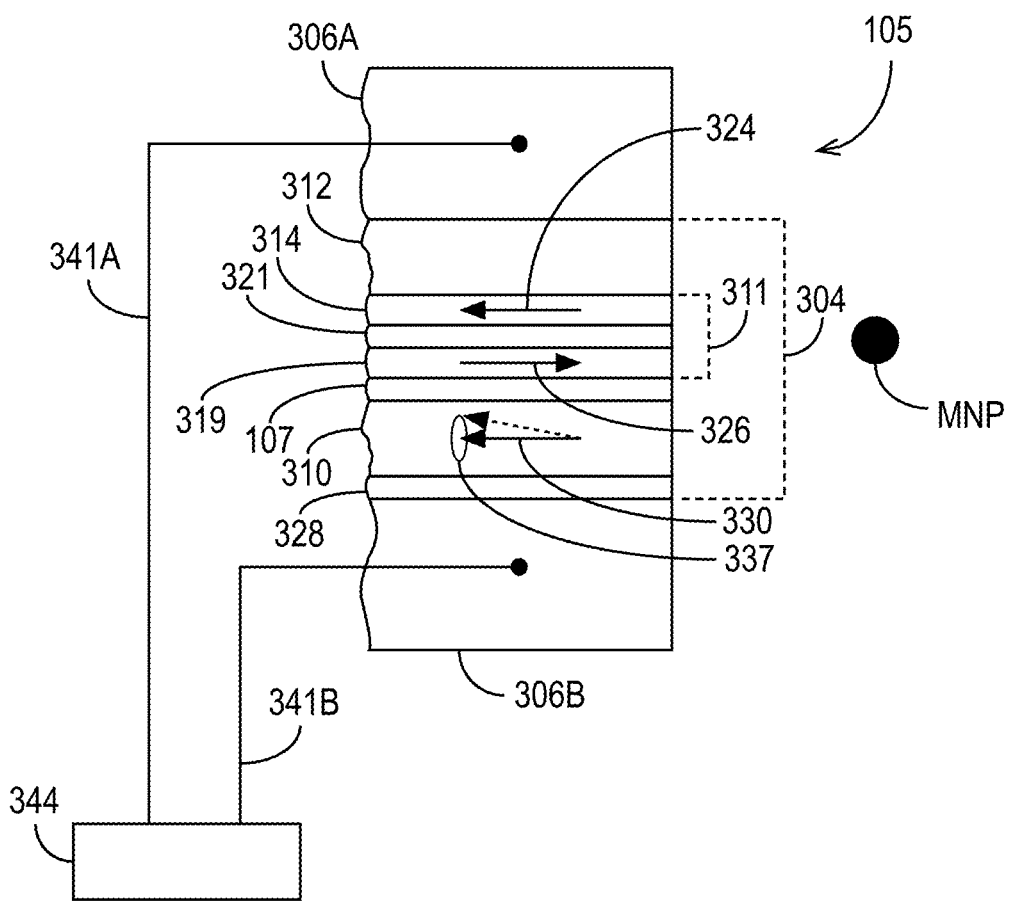
FIG. 1B illustrates an exemplary sensor that can take advantage of spin torque oscillations to sense a localized magnetic field caused by a magnetic particle in accordance with some embodiments.

FIG. 1B is a view of another exemplary sensor 105 that can take advantage of spin torque oscillations to sense a localized magnetic field caused by a magnetic particle (e.g., a MNP). FIG. 1B shows a cross-sectional view of the sensor 105 with the MNP being sensed shown located to the right of the sensor 105.

The exemplary sensor 105 of FIG. 1B includes a sensor stack 304 that is sandwiched between optional first and second magnetic shields 306A, 306B. If present, the magnetic shields 306A, 306B can be made of an electrically conductive, magnetic material such as NiFe so that they can function as electrical leads as well as magnetic shields. The sensor stack 304 includes a pinned layer structure 311, a free layer 310, and a non-magnetic spacer layer 107 sandwiched between the free layer 310 and the pinned layer structure 311. As explained above in the context of FIG. 1A, the non-magnetic spacer layer 107 can be a non-magnetic, electrically conducting spacer layer, or it can be a thin, non-magnetic, electrically-insulating barrier layer. A capping layer 328 (e.g., comprising tantalum) can be situated adjacent to the free layer 310 as shown in FIG. 1B. It is to be appreciated that FIG. 1B shows the sensor 105 with an exemplary orientation of layers (e.g., the pinned layer structure 311 above the free layer 310), but that other orientations are possible (e.g., the pinned layer structure 311 can be below the free layer 310, the sensor 105 can be rotated relative to how it is shown in FIG. 1B, some of the elements shown in FIG. 1B (e.g., shields 306A, 306B) can be omitted, etc.).

The pinned layer structure 311 can include a magnetic pinned layer 314, a reference layer 319, and a non-magnetic antiparallel coupling layer 321 sandwiched between the pinned layer 314 and the reference layer 319. The pinned and reference layers 314, 319 can comprise a material such as, for example, CoFe, and the antiparallel coupling layer 321 can comprise a material such as, for example, Ru having a thickness of, for example, about 10 Angstroms. The pinned layer 314 can be exchange coupled with a layer of antiferromagnetic material, AFM layer 312, which can comprise a material such as, for example, IrMn, PtMn, or some other suitable antiferromagnetic material as is known in the art. Exchange coupling between the AFM layer 312 and the pinned layer 314 strongly pins the magnetization 324 of the pinned layer 314 in a first direction as indicated. Strong antiparallel coupling between the pinned and reference layers 314, 319 pins the magnetization 326 of the reference layer 319 in a second (antiparallel) direction as indicated.

In the exemplary embodiment shown in FIG. 1B, the free layer 310 has its magnetization 330 biased in a direction that is substantially anti-parallel to the magnetization 326 of the reference layer 319. In some embodiments, in the quiescent state of the magnetization (e.g., when the STO is not oscillating), the magnetization 330 of the free layer 310 is at a modest angle relative to the magnetization 326 of the reference layer 319. This can be seen with reference to FIG. 1C, which shows an exploded schematic view of the reference layer 319 and free layer 310, which are shown offset. As shown, the reference layer 319 has a magnetization 326 that is pinned in a direction that is parallel (but could alternatively be antiparallel) to an applied magnetic field 327, but the free layer 310 has a magnetization 330 that is biased in a direction that is nearly antiparallel to the direction of the reference layer magnetization 326, but is offset by an angle 329. The angle 329, if present, is generally about 20-60 degrees but may be as large as nearly 90 degrees. Biasing of the free layer 310 can be provided by hard magnetic bias layers that are not shown in FIG. 1B, but would be into and out of the page in FIG. 1B. While the free layer 310 is magnetically biased, the magnetization 330 of the free layer 310 is free to move in a precessional spin torque oscillation 337 as indicated in FIG. 1B and as discussed previously.

With reference again to FIG. 1C, canting of the free layer 310 magnetization 330 direction with respect to the magnetization 326 direction of the reference layer 319 can be provided by a magnetic anisotropy having a component oriented perpendicular to the direction of magnetization 326 of the reference layer 319, and/or perpendicular to a direction of an applied magnetic field 327. This magnetic anisotropy can be produced by a layer of antiferromagnetic material that is weakly exchange coupled with the free layer 310, or by shape anisotropy, or by a texture induced magnetic anisotropy. The canting of the free layer 310 can also be achieved by placement of high coercivity magnetic material near the free layer 310 and with magnetization having a substantial component perpendicular to the reference layer 319, in analogy to the hard bias structures that may be used in recording heads to stabilize the free layer of GMR and TMR readback sensors. These are by way of example, however; other mechanisms could be used as well.

As described in further detail below, when a high current density of spin-polarized electrons generated by one magnetized layer impinges upon a second magnetized layer, spin torque effects are observed, and these spin torque effects dynamically excite the second layer's magnetization through a mechanism called spin transfer. Here, electrons traveling through the ferromagnet tend to have their spins aligned parallel to the magnetization of the ferromagnet, losing any component of spin angular momentum transverse to the magnetization. To conserve angular momentum, the polarized current must then exert a torque upon the magnetization.

Figure 2A:
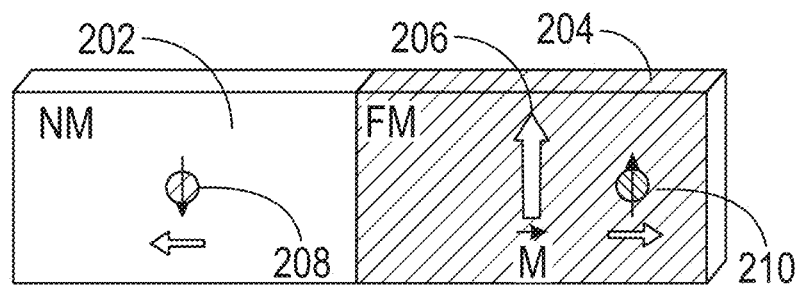
FIGS. 2A, 2B, and 2C illustrate how electrons in an electric current interact with thin-film ferromagnetic layers in accordance with some embodiments.
Figure 2B:
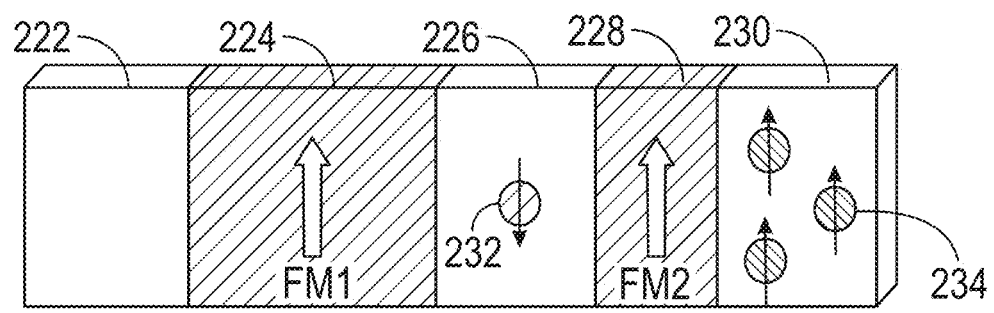
Figure 2C:
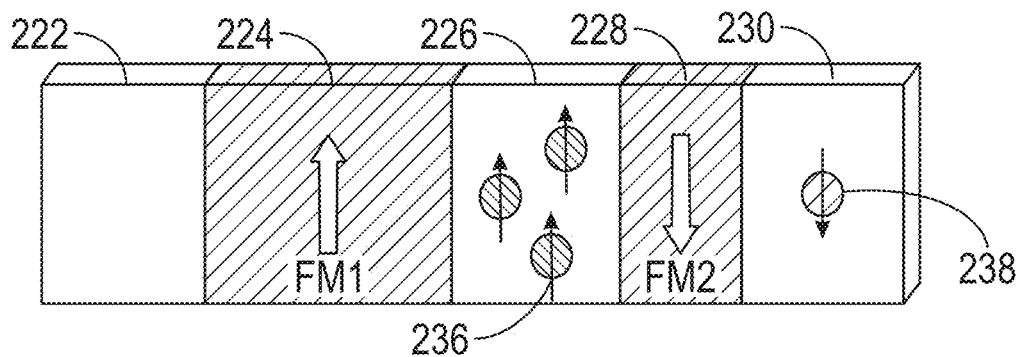

FIGS. 2A through 2C illustrate in further detail how an electron in an electric current interacts with thin-film FM layers. Quantum mechanics dictate that the probability is high that an electron interacting with a FM layer will cause the electron spin to be oriented preferentially parallel or antiparallel to the direction of the FM layer's moment for transmitted and reflected electrons respectively. As shown in FIG. 2A, electrons with spin 210, which is parallel to the moment 206 of the FM layer 204, preferentially pass through the FM layer 204, whereas those with spin 208, which is antiparallel to the moment 206 of the FM layer 204, preferentially are reflected back. Due to this phenomenon, the interface between a nonmagnetic (NM) layer 202 (assumed for purposes of this explanation to be a metal layer, although, as discussed above, the NM layer 202 may alternatively be an insulator) and a FM layer 204 acts as a spin filter that can act to spin polarize (i.e., make one spin direction more preferential) an incoming electric current.

For a device with two FM layers 224 and 228 separated by a nonmagnetic metal layer 226 (spacer layer), as shown in FIGS. 2B and 2C, an incoming electric current spin polarized by the first FM layer (FM1) 224 interacts differently with the second FM layer (FM2) 228, depending on the orientation of the second FM layer 228's magnetic moment. If the moments of both FM layers 224 and 228 are parallel to one another (FIG. 2B), then many electrons will pass through the device because many electrons in the current will have their spin oriented with the moment of the second FM layer 228 (spin 234). Few electrons will be reflected back (spin 232).

If, on the other hand, the moments of the two FM layers 224 and 228 are oriented in an anti-parallel fashion (FIG. 2C), many electrons will be blocked from passing through the second FM layer 228 (spin 236), and far fewer electrons will traverse the device (spin 238). This means the amount of current passing through the device is dependent on the orientation of the moments of the two FM layers 224 and 228 with respect to one another. Because the resistance of the device that includes FM layers 224 and 228 and NM layer 226 is inversely proportional to the current, the resistance of the device is dependent on the orientation of the moments of the two FM layers 224 and 228 (i.e., the resistance is smaller when the moments are parallel than it is when they are antiparallel).

Whereas the above description presumes use of a nonmagnetic metal layer 226 separating the two FM layers 224 and 228 (a configuration also known as a spin valve (SV) or giant magnetoresistance (GMR) device), an insulating layer known as a tunneling barrier can alternatively be used as the spacer layer (e.g., instead of NM layer 226) separating the FM layers 224, 228. In such implementations, the spacer layer may be made of oxide-based material. These types of devices are called magnetic tunnel junctions (MTJs), and they exhibit a similar resistance response (referred to as tunnel magnetoresistance or TMR) because of spin polarized tunneling as opposed to spin filtering.

FIGS. 3A through 3C further illustrate the basic operating principles of STO-based sensors 105. FIG. 3A shows how incident electrons 904 with arbitrary spin direction either transmit through or are reflected by a FM layer 906. As shown, those incident electrons 904 with spin parallel to the magnetic moment of the FM layer 906 are transmitted electrons 908, whereas incident electrons 904 with spin anti-parallel to the magnetic moment of the FM layer 906 are reflected electrons 902. Any spin angular momentum lost becomes a torque acting on the FM layer 906. The torque from a single electron interaction is small, but for a spin polarized current on the order of a milli-Ampere, there are approximately $10^{15}$ electrons interacting with the FM layer 906 per second. Thus, the net torque on the FM layer 906 can be sufficient to induce the moment into a dynamic mode. These dynamics are governed by the Landau-Lifshitz-Gilbert-Slonczewski (LLGS) equation:

$$\frac{d\hat{m}}{dt} = -\gamma \hat{m} \times \vec{H}_{eff} + \alpha \hat{m} \times \frac{d\hat{m}}{dt} + \frac{\eta I}{|m|} \hat{m} \times \hat{p} \times \hat{m}$$

where $\gamma$ is the gyromagnetic ratio, $\hat{m}$ is the normalized moment vector, $\vec{H}_{eff}$ is the effective magnetic field acting on the FM layer 906, $\alpha$ is the phenomenological Gilbert damping parameter, $\eta$ is spin polarization of the current I, and $\hat{p}$ is the direction of the current's spin polarization.

The first term in the equation, called the Larmor precession term, indicates that in the absence of any damping, the moment of the FM layer 906 will precess around the effective magnetic field acting on the FM layer 906. However, the second term (Gilbert damping) comes from intrinsic damping occurring in every ferromagnet that acts to damp out any dynamics of the moment. The final term is the Slonczewski spin torque term that acts like either a damping or anti-damping term, depending on the polarity of the applied electric current. In the case of anti-damping, the spin torque will entirely cancel out the Gilbert damping at a sufficient current amplitude and will result in magnetization oscillations as shown in FIG. 3C. As the current amplitude further increases, the oscillation amplitude also increases, eventually causing the moment to cross points 90 degrees from equilibrium. In this region, the cross product in the Slonczewski term changes sign and acts to damp out the motion such that the moment will rotate 180 degrees from the original position, as shown in FIG. 3B.

Thus, considering a full STO device similar to that described above, with one FM layer 906 excited through spin transfer effects and a second FM layer 906 with a moment fixed in some chosen direction (they are co-linear), a STO excited as shown in FIG. 3C will produce a radio-frequency (RF) voltage signal from an applied DC current due to resistance fluctuations (and, therefore, voltage and current fluctuations) caused by magnetoresistive effects. The frequency of the generated RF signal can be on the order of GHz.

Referring again to FIG. 1B, with electrons flowing from the reference layer 319 through the non-magnetic spacer layer 107 to the free layer 310, the spin of the electrons flowing through the reference layer 319 are polarized by the magnetization 326 of the reference layer 319. These polarized electrons can then apply a torque to the free layer magnetization 330, generating spin waves that result in chaotic magnetization dynamics (noise) or collective excitations (oscillations), depending on various parameters of the system such as sensor 105 shape, anisotropy, layer materials and thicknesses, and applied currents and magnetic fields.

As explained above, spin torque oscillations involve spin-torque-excited precession of the magnetization along the equilibrium axis of the ferromagnet. For example, with reference to FIG. 1B, the precession, or oscillation, of the magnetization 330 is indicated by oscillation 337. Note that although the pinned layer 314 magnetization 324 is constrained by exchange anisotropy to an antiferromagnetic layer 312, it is possible for the magnetization of the pinned layer 314 to oscillate as well, and to contribute to the sensor 105 signal when the applied current densities are high enough to generate spin torque excitations in the pinned layer 314.

The frequency of this precession (oscillation frequency) shifts with the application of a magnetic field. With a suitable selection of sensor materials and geometry, this shift can be very large. Frequency shifts up to 180 GHz/T have been demonstrated, and higher values are possible. Some embodiments described herein take advantage of these frequency shifts to detect the change in magnetic field at the free layer 310 induced by magnetic nanoparticles in the vicinity of the sensor 105.

Referring to FIG. 1B, the sensor 105 is connected via leads 341A, 341B to processing circuitry 344. The leads 341A, 341B, which may be magnetic or nonmagnetic, can be connected with the optional shield/lead layers 306A, 306B (if present) such that one lead 341A is connected with one lead/shield layer 306A, while the other lead 341B is connected with the other lead/shield layer 306B. The processing circuitry 344 sends a sense (bias) current through the sensor stack 304 and also measures the electrical resistance across the sensor stack 304. As those skilled in the art will appreciate, the electrical resistance across the nonmagnetic spacer layer 107 changes as the orientation of the magnetization 330 of the free layer 310 changes relative to the magnetization 326 of the reference layer 319. As explained above, the closer these magnetizations 330, 326 are to being parallel, the lower the electrical resistance will be. Conversely, the closer these magnetizations 330, 326 are to being anti-parallel, the higher the electrical resistance will be. The resistance of the device effectively acts as a magnetic-field-to-voltage transducer.

The presence of a MNP in the vicinity of the sensor 105 causes the above-described change in the frequency of the oscillation 337 of the magnetization 330. As the magnetization 330 oscillates, the frequency of this oscillation 337 can be measured by the processing circuitry 344 by measuring the change of electrical resistance across the sensor stack 304. In addition or alternatively, a change in the frequency of oscillation 337 can be detected to determine whether a MNP is in the vicinity of the sensor 105. In addition or alternatively, the noisiness of the oscillation frequency can be detected and/or monitored. The frequency noise is expected to be larger in the presence of one or more MNPs than in the absence of any MNPs. Therefore, in accordance with some embodiments disclosed herein, the spin torque oscillation is used to detect the presence or absence of magnetic nanoparticles in the vicinity of a sensor 105.

Figure 1C:
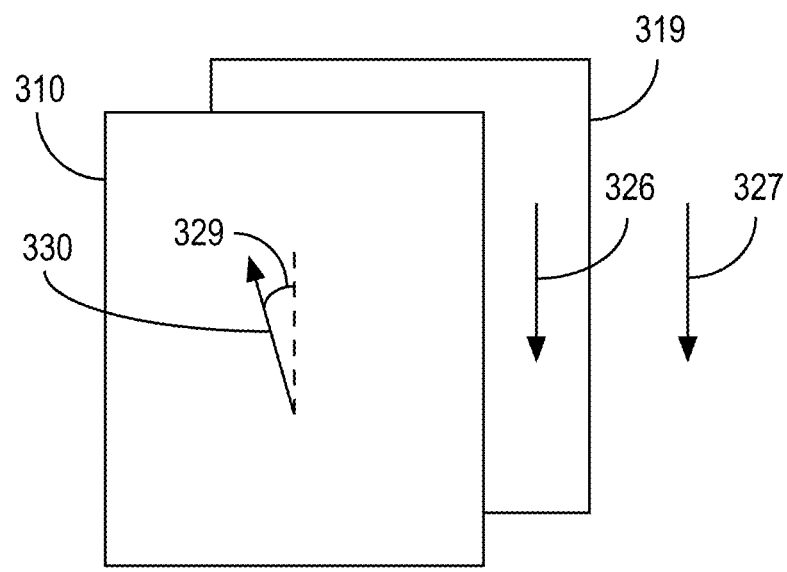
FIG. 1C shows an exploded schematic view of a sensor's reference layer and free layer in accordance with some embodiments.

Taking advantage of the operational principles of STOs for detection, some embodiments disclosed herein involve an array of sensors 105 comprising STO devices, such as the sensors 105 shown in FIGS. 1A, 1B, and 1C and the arrays shown in, for example, FIGS. 4A-4C, 5A-5D, etc. Each of the sensors 105 of the sensor array may be used to detect magnetic particles (e.g., MNPs) in a fluidic channel of a detection device. Each sensor 105 may have dimensions of less than about 30 nm to detect magnetic fields on the order of a few tens of Oersted (Oe). In some embodiments, individual sensors 105 in a sensor array are configured to generate a RF signal only within a narrow band of magnetic fields (e.g., around zero applied field, although that is not required), for example between 50 and −50 Oe.

In DNA sequencing applications, nucleotide precursors (or, more generally, nucleic acids) labeled by MNPs and incorporated by polymerase in the vicinity of a sensor 105 may be detected by assessing the phase noise of the sensor 105. For example, in some embodiments, the sensor 105 generates a RF signal at or near a particular frequency in the absence of a MNP, and it continues to generate a RF signal at or near the particular frequency in the presence of a MNP, but with a higher phase noise due to the presence of the MNP. In some embodiments, the MNPs are superparamagnetic and have an impact on the phase noise of the RF signal generated by a sensor 105 in the absence of an applied (e.g., external) magnetic field. In other embodiments, the MNPs are not superparamagnetic, and an applied (e.g., external) magnetic field is applied to detect whether the MNPs are affecting the phase noise of the RF signal generated by the sensor. By monitoring the phase noise of the RF signal generated by the MNP, the presence or absence of MNPs can be detected (e.g., when the phase noise is below a threshold, it can be inferred that there are no MNPs present, and when the phase noise is above the threshold, it can be inferred that one or more MNPs are in the vicinity of a sensor and are the cause of the phase noise).

An advantage of performing detection using sensors 105 comprising STO devices is that, as discussed in further detail below, the MNPs used as labels may be either superparamagnetic (e.g., thermally unstable such that the magnetic field generated fluctuates over time) or ferromagnetic. Moreover, the use of STOs does not require the moments of individual MNPs to be aligned in the same direction (e.g., detection may be accomplished with or without use of an external magnetic field). One benefit of superparamagnetic particles is that they are not ferromagnetic and will not stick to or attract each other appreciably when introduced into a flow cell of a detection device (e.g., the fluidic channels described below in the context of, e.g., FIGS. 4A-4C and 5A-5D). Additionally, the use of superparamagnetic particles is attractive because the effect of superparamagnetic particles on the noise of STO oscillations can be detected without use of an external applied magnetic field.

Detection Devices

Figure 4A:
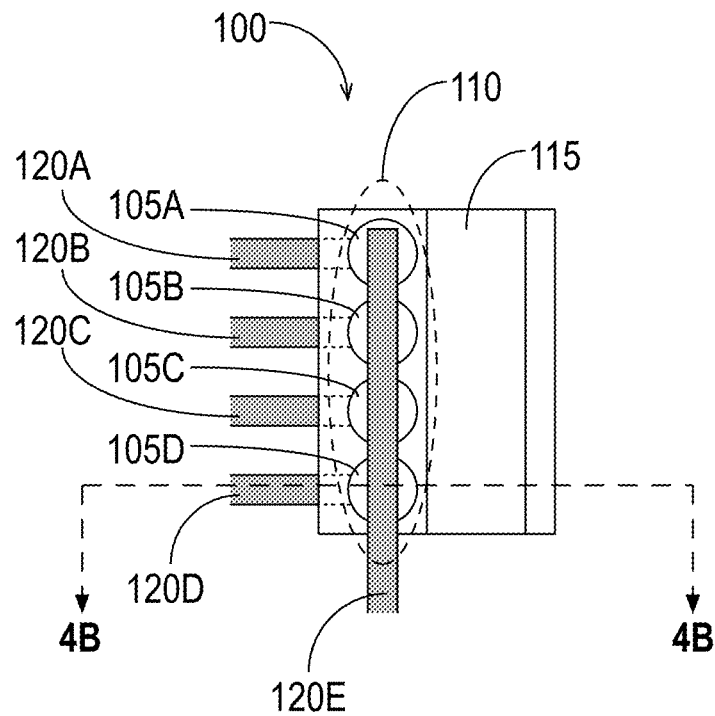
FIGS. 4A, 4B, and 4C illustrate an apparatus for molecule detection in accordance with some embodiments.
Figure 4B:
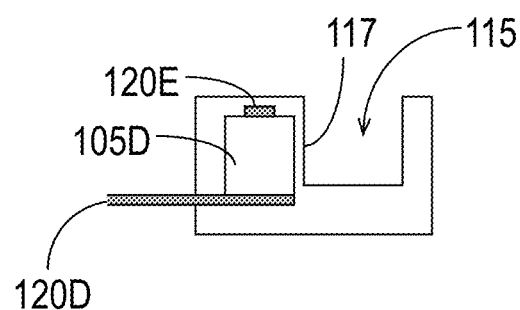
Figure 4C:
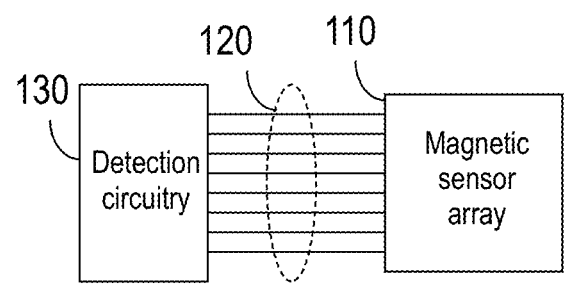

The STO-based sensors 105 described above may be incorporated into an apparatus for the detection of molecules that are coupled to respective magnetic nanoparticles (e.g., for nucleic acid sequencing). FIGS. 4A, 4B, and 4C illustrate a detection device 100 that may be used, for example, for nucleic acid sequencing in accordance with some embodiments. FIG. 4A is a top view of the apparatus, and FIG. 4B is a cross-section view at the position labeled "4B" in FIG. 4A. FIG. 4C is a block diagram showing components of the detection device 100. As shown in FIG. 4A, the exemplary detection device 100 comprises a sensor array 110 that includes a plurality of sensors 105, with four sensors 105A, 105B, 105C, and 105D shown. (For simplicity, this document refers generally to the sensors by the reference number 105. Individual sensors are given the reference number 105 followed by a letter.) The sensor array 110 shown in the exemplary embodiment of FIG. 4A is a linear array.

In some embodiments, each of the plurality of sensors 105 is coupled to at least one line 120 for reading a characteristic of or output from one or more of the sensors 105 (e.g., determining whether a sensor 105 is oscillating at a particular frequency, detecting a phase noise of a RF signal generated by a sensor 105, etc.). (For simplicity, this document refers generally to the lines by the reference number 120. Individual lines are given the reference number 120 followed by a letter.) In the exemplary embodiment shown in FIG. 4A, each sensor 105 of the sensor array 110 is coupled to two lines 120. Specifically, the sensor 105A is coupled to the lines 120A and 120E, the sensor 105B is coupled to the lines 120B and 120E, the sensor 105C is coupled to the lines 120C and 120E, and the sensor 105D is coupled to the lines 120D and 120E. The lines 120A, 120B, 120C, and 120D reside under the sensors 105A, 105B, 105C, and 105D, respectively, and the line 120E resides over the sensors 105. FIG. 4B shows the sensor 105D in relation to the lines 120D and 120E.

The detection device 100 also includes a fluidic channel 115 (which may also be referred to as a nanochannel or flow cell) that is adjacent to the sensor array 110. As its name suggests, the fluidic channel 115 is configured to hold fluids (e.g., liquids, gases, plasmas) when the detection device 100 is in use. The fluidic channel 115 may by open (e.g., if its shape is rectangular, it may have three sides; if its shape is curved, it may have a shape that is a portion of a cylinder; etc.) or closed (e.g., if its shape is rectangular, it may have four sides; if its shape is curved, it may be cylindrical; etc.). The shape of the fluidic channel 115 may be regular or irregular along its length. The fluidic channel 115 may be coupled to a device (e.g., a pump) that forces fluids into the fluidic channel 115. Alternatively, the fluidic channel 115 may not be coupled to a device that injects or removes fluids.

As shown in FIG. 4B, the fluidic channel 115 has a wall 117 that is adjacent to the sensor array 110. The wall 117 may be referred to as a proximal wall. The wall 117 may be substantially vertical as illustrated in FIG. 4B. Alternatively, the wall 117 may be sloped at least in part (e.g., some or all of the interior of the fluidic channel 115 may be at an angle that is not 90 degrees, or it may be curved (e.g., in the shape of a portion or all of a cylinder)). In general, the fluidic channel 115 and wall 117 may have any shapes that allow the sensors 105 to detect the presence of magnetic particles on the other side of the wall 117 that are within the fluidic channel 115.

When the detection device 100 is in use, the sensors 105 are able to detect, through the wall 117, the presence or absence of MNPs that are in the fluidic channel 115. Thus, the wall 117 has properties and characteristics that protect the sensors 105 from whatever fluid is in the fluidic channel 115 while still allowing the sensors 105 to detect MNPs that are within the fluidic channel 115. For example, the material of the wall 117 (and potentially of the rest of the fluidic channel 115) may be or comprise an insulator material. For example, in some embodiments, a surface of the wall 117 comprises polypropylene, gold, glass, and/or silicon. In addition, the thickness of the wall 117 may be selected so that the sensors 105 can detect MNPs within the fluidic channel 115. In some embodiments, the thickness of the wall 117 is between approximately 2 nm and approximately 20 nm.

In some embodiments, the wall 117 has a structure (or multiple structures) configured to anchor or bind molecules to be sensed (e.g., nucleic acid or molecules of a nucleic acid polymerase) to the wall 117. For example, the structure (or structures) of the wall 117 may include a cavity or a ridge or multiple cavities/ridges that provide binding sites associated with the sensors 105.

To simplify the explanation, FIGS. 4A and 4B illustrate an exemplary detection device 100 with a single fluidic channel 115 and only four sensors 105A, 105B, 105C, 105D in the sensor array 110. It is to be appreciated that the detection device 100 may have many more sensors 105 in the sensor array 110, and it may have either additional fluidic channels 115 or a more intricate single fluidic channel 115 (e.g., with a different shape or with interconnected channels). In general, any configuration of sensors 105 and fluidic channel(s) 115 that allows the sensors 105 to detect MNPs in the fluidic channel(s) 115 may be used.

As illustrated in FIG. 4C, the detection device 100 includes detection circuitry 130 coupled to the sensor array 110 via the lines 120. In some embodiments, in operation, the detection circuitry 130 applies a current to the lines 120 to detect a characteristic of or output from at least one of the plurality of sensors 105 in the sensor array 110, where the characteristic or output indicates a presence or an absence of a magnetically-labeled molecule in the fluidic channel 115. For example, in some embodiments, the characteristic or output is a signal or an absence of a signal. In other embodiments, the characteristic is the oscillation frequency or frequency noise of a signal. The detection circuitry 130 may comprise any suitable components, including, generally, suitable detection circuitry. Such detection circuitry 130 may comprise hardware and/or software. The detection circuitry 130 may include, for example, one or more of: a processor capable of executing machine-executable instructions, an application-specific integrated circuit (ASIC), a controller, a programmable circuit (e.g., FPGA), etc.

As an example of a detection device 100 with a larger number of sensors 105 in the sensor array 110, FIGS. 5A, 5B, 5C, and 5D illustrate portions of an exemplary detection device 100 that includes several channels, one or more of which may be a separate fluidic channel 115 in accordance with some embodiments, or the aggregation of which may be considered a single fluidic channel 115. In the embodiment of the detection device 100 shown in FIGS. 5A, 5B, 5C, and 5D, the plurality of sensors 105 of the sensor array 110 is arranged in a rectangular grid pattern. Each of the lines 120 identifies a row or a column of the sensor array 110. It is to be understood that FIGS. 5A, 5B, 5C, and 5D show only a portion of the detection device 100 to avoid obscuring the parts of the detection device 100 being discussed. It is to be understood that the various illustrated components (e.g., lines 120, sensors 105, fluidic channels 115, etc.) might not be visible in a physical instantiation of the detection device 100 (e.g., some or all may be covered by protective material, such as an insulator material).

Figure 5A:
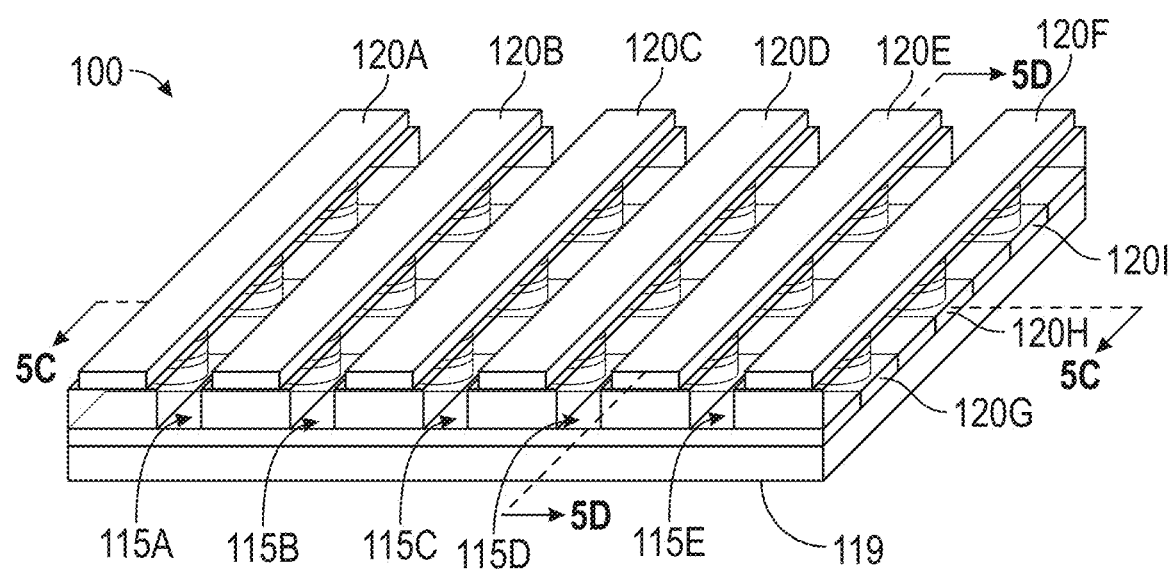
FIGS. 5A, 5B, 5C, and 5D illustrate portions of another exemplary apparatus for molecule detection in accordance with some embodiments.

FIG. 5A is a perspective view of the exemplary detection device 100 in accordance with some embodiments. The detection device 100 includes nine lines 120, labeled as 120A, 120B, 120C, 120D, 120E, 120F, 120G, 120H, and 120I. It also includes five fluidic channels, labeled as 115A, 115B, 115C, 115D, and 115E. As explained above, the fluidic channels 115A, 115B, 115C, 115D, and 115E may be considered to be separate fluidic channels 115 or a single fluidic channel 115. The detection device 100 also has a bottom surface 119.

Figure 5B:
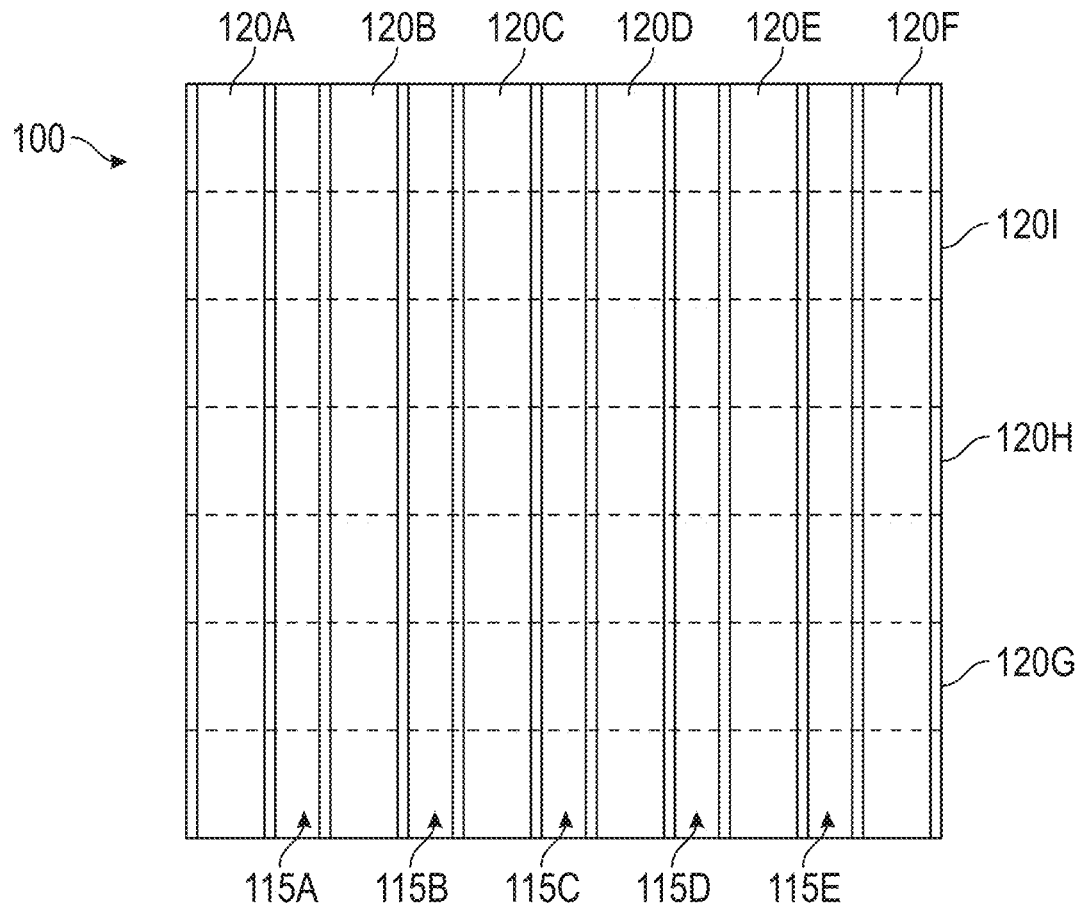

FIG. 5B is a top view of the exemplary detection device 100 from FIG. 5A. The lines 120G, 120H, and 120I, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator material).

Figure 5C:
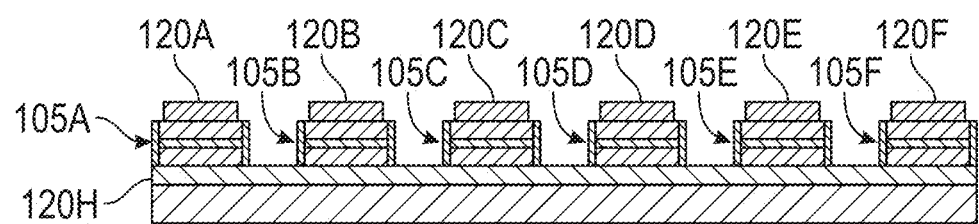

FIG. 5C is a cross-sectional view of the detection device 100 along the line labeled "5C" in FIG. 5A. As shown, each of the lines 120A, 120B, 120C, 120D, 120E, and 120F is in contact with the top of one of the sensors 105 along the cross-section (namely, line 120A is in contact with sensor 105A, line 120B is in contact with sensor 105B, line 120C is in contact with sensor 105C, line 120D is in contact with sensor 105D, line 120E is in contact with sensor 105E, and line 120F is in contact with sensor 105F). The line 120H is in contact with the bottom of each of the sensors 105A, 105B, 105C, 105D, 105E, and 105F. It is to be appreciated that although FIGS. 5A-5D illustrate the lines 120 in contact with the sensors 105, the lines 120 may, in general, be coupled to the sensors 105 (i.e., they may be directly connected, or there may be intervening components disposed between the lines 120 and the sensors 105).

The sensors 105A and 105B are separated by the fluidic channel 115A (unlabeled in FIG. 5C but shown in FIG. 5A). Similarly, the sensors 105B and 105C are separated by the fluidic channel 115B, the sensors 105C and 105D are separated by the fluidic channel 115C, the sensors 105D and 105E are separated by the fluidic channel 115D, and the sensors 105E and 105F are separated by the fluidic channel 115E. As discussed further below, either or both of the vertical walls of each fluidic channel 115 may be the wall 117.

In some embodiments, each sensor 105 is assigned to a single fluidic channel 115. For example, in the exemplary device illustrated in FIGS. 5A-5D, the sensors 105 coupled to the line 120A may be configured to sense MNPs in the fluidic channel 115A, the sensors 105 coupled to the line 120B may be configured to sense MNPs in the fluidic channel 115B, the sensors 105 coupled to the line 120C may be configured to sense MNPs in the fluidic channel 115C, the sensors 105 coupled to the line 120D may be configured to sense MNPs in the fluidic channel 115D, and the sensors 105 coupled to the line 120E may be configured to sense MNPs in the fluidic channel 115E.

In the exemplary embodiment illustrated in FIGS. 5A-5C, there are more columns of sensors 105 than there are fluidic channels 115 (i.e., in the exemplary embodiment shown, there are six columns corresponding to lines 120A-120F and only five fluidic channels 115A-115E). In such embodiments, each vertical wall of one fluidic channel 115 may be the wall 117. In other words, a single fluidic channel 115 may be sensed by twice as many sensors 105 as each of the other fluidic channels 115. For example, in the exemplary embodiment of FIGS. 5A-5D, any of the fluidic channels 115 may be sensed by two columns of sensors 105. For example, the fluidic channel 115B may be sensed by the sensors 105 coupled to both lines 120B and 120C. In this example, the sensors 105 coupled to the line 120A would be assigned to sense the contents of the fluidic channel 120A, the sensors 105 coupled to the line 120D would be assigned to sense the contents of the fluidic channel 120C, the sensors 105 coupled to the line 120E would be assigned to sense the contents of the fluidic channel 120D, and the sensors 105 coupled to the line 120F would be assigned to sense the contents of the fluidic channel 120E.

Figure 5D:
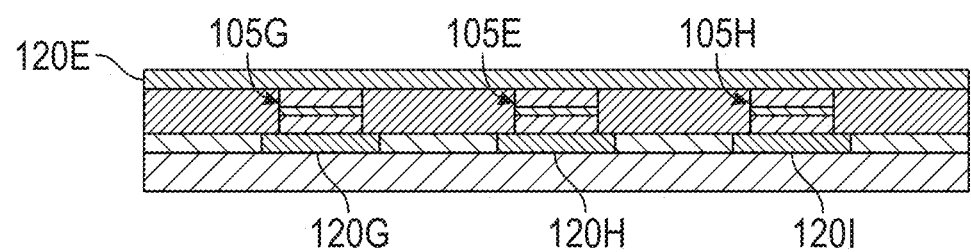

FIG. 5D is a cross-sectional view of the detection device 100 along the line labeled "5D" in FIG. 5A. As shown, the line 120E is in contact with the top of each of the sensors 105G, 105E, and 105H along the cross-section. Each of the lines 120G, 120H, and 120I is in contact with the bottom of one of the sensors 105 along the cross-section (namely, line 120G is in contact with sensor 105G, line 120H is in contact with sensor 105E, and line 120I is in contact with sensor 105H). As explained above, the lines 120 shown in FIG. 5D need not be in direct contact with the sensors 105; instead, they may be connected through intervening components.

In some embodiments (see, e.g., FIGS. 5E, 5F), the detection device 100 includes a plurality of selector elements 111, each of which is coupled to a respective one of the sensors 105, where each of the selector elements 111 exhibits thresholding behavior such that for voltages above a given value (i.e., $V_{th}$) the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the sensors 105 (individually or in groups) can be used that ensure only the voltage dropped across the intended sensor (s) 105 is above $V_{th}$. Accordingly, selector elements 111 may be used reduce the chances of "sneak" currents that could transmit through neighboring elements and degrade the performance of the detection device 100.

Figure 5E:
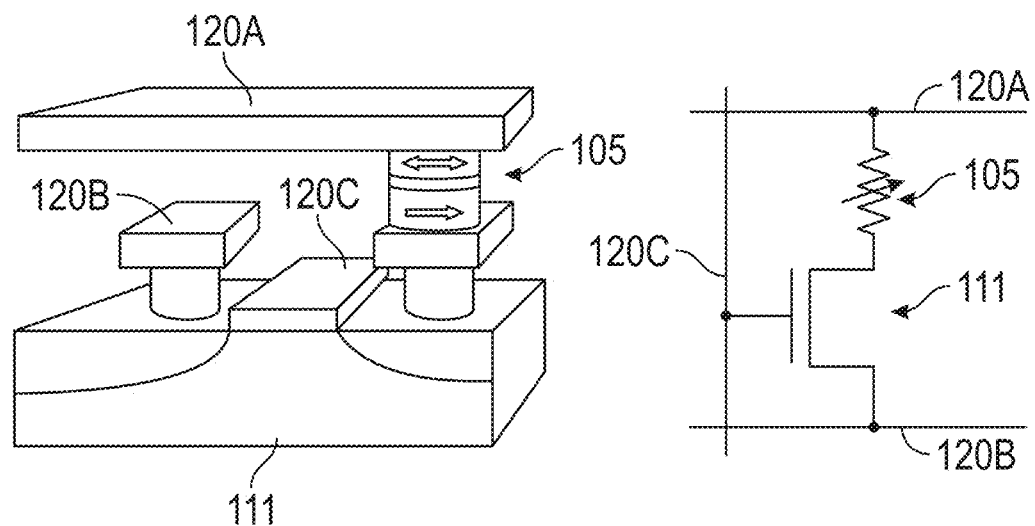
FIG. 5E illustrates a sensor selection approach in accordance with some embodiments.

FIG. 5E illustrates an exemplary sensor 105 selection approach in accordance with some embodiments. In the exemplary embodiment shown in FIG. 5E, a respective selector element 111 (e.g., shown as a CMOS transistor) is coupled in series with the sensor 105. In this exemplary embodiment, three lines 120A, 120B, and 120C allow a characteristic of the sensor 105 to be sensed. Conceptually, the line 120A may be considered to be a read-out line, the line 120C may be considered to be a control line, and the line 120B may be considered to be either or both a read-out line and a control line. For more detail on configurations such as the exemplary one shown in FIG. 5E, see B. N. Engel, J. Akerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAIVI Based on a Novel Bit and Switching Method," IEEE Transactions on Magnetics, Vol. 41, 132 (2005).

Figure 5F:
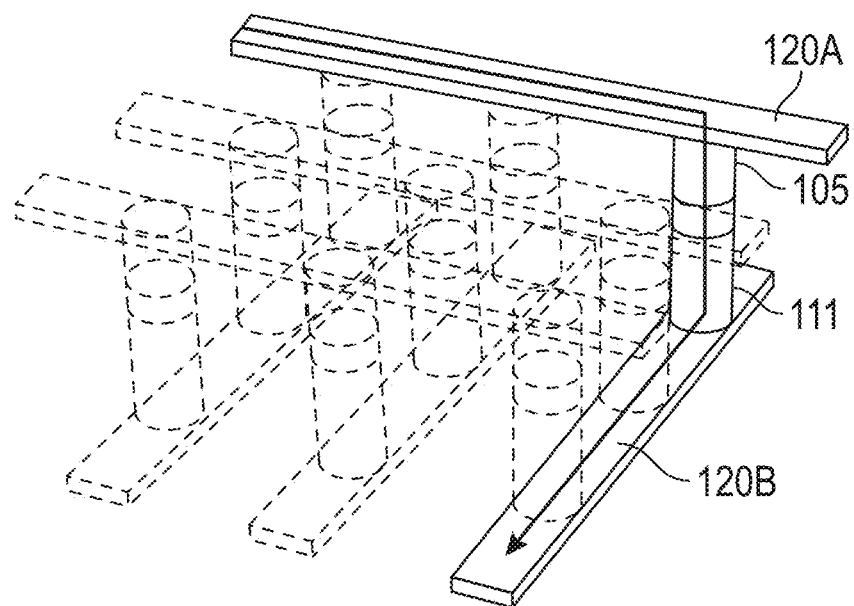
FIG. 5F illustrates another sensor selection approach in accordance with some embodiments.

FIG. 5F illustrates another exemplary sensor 105 selection approach in accordance with some embodiments. In the exemplary embodiment shown in FIG. 5F, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with the magnetic films of the sensors 105 and then placed into a cross-point architecture. Although FIG. 5F shows the in-stack selector elements 111 below the sensors 105, it is to be understood that the order of the in-stack selector elements 111 and the sensors 105 may be reversed. Respective selector devices (e.g., CMOS transistors) may be used to turn on the individual lines 120A, 120B to address/access individual sensors 105 in the detection device 100. The use of CMOS select transistors may be simple due to the prevalence of foundries available to fabricate the front end (i.e., the nanofabrication to build the CMOS transistors and underlying circuitry), but the types of currents used for operation may use a cross-point design to eventually reach the densities desired. Additional details on configurations suitable to select sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

FIGS. 6A through 6C illustrate an embodiment of a cross-point array architecture 300 that may be included in the detection device 100 in accordance with some embodiments. For illustration, the sensors 105 illustrated in FIGS. 6A through 6C comprise MTJ elements 308, but it is to be appreciated that, as explained above, some or all of the sensors 105 may be spin valves.

Referring to FIG. 6A, the cross-point array architecture 300 includes top wires 318 and bottom wires 320. As shown in the exemplary embodiment of FIG. 6A, the top wires 318 are oriented substantially perpendicularly to (at approximately 90 degree angles from) the bottom wires 320. An example MTJ element 308 (e.g., a sensor 105) is situated between a crossing of the array (dashed circle). The example MTJ element 308 includes two or more FM layers 310, 314 separated by one or more non-magnetic layers 107 (e.g., comprising MgO). As shown, one of the FM layers is a free layer 310 that will rotate in the presence of a magnetic field, and another of the FM layers is a pinned (or fixed) layer 314 that may be a single FM layer coupled to an AFM layer 312. Alternatively, a compound structure called a synthetic antiferromagnet (SAF) may be used. The SAF includes two FM layers separated by a magnetic coupling layer (e.g., ruthenium), with one of the two FM layers coupled to an AFM layer. It is to be understood that although the example layer arrangement of MTJ element 308 shows a general structure with layers over or under other layers, intervening layers not shown can be inserted. Moreover, as discussed above, additional layers may be disposed above and/or below the illustrated structure.

To illustrate some of the features of the cross-point array architecture 300, FIG. 6B shows a cross-section of the cross-point array architecture 300 along the top wire 318 direction (indicated in FIG. 6A by the dash-dot line labeled "6B"), and FIG. 6C shows a cross-section of the cross-point array architecture 300 along the bottom wire 320 direction (indicated in FIG. 6A by the dashed line labeled "6C"). As shown, the sides of the MTJ elements 308 (the sensors 105) are encapsulated by material 336, which may be an insulator. Optionally, as shown in FIG. 6B, a hard bias magnetic material 338 may also be deposited between the MTJ elements 308. In embodiments including hard bias magnetic material 338, a thin layer of insulator 340 is also deposited on top of the hard bias magnetic material 338 to electrically insulate it from the top wire(s) 318.

Referring to FIG. 6C, the cross section shows the fluidic channels 115 (e.g., nanofluidic or microfluidic channels), which may be, for example, trenches etched in an insulator. As shown, a small amount of insulator 322 is left on the sidewalls of the sensors 105 (illustrated as MTJ elements 308) so that the MNPs do not electrically interact with the sensors 105. The portion of the insulator exposed to (and forming) the fluidic channel 115 may form the wall 117 to which polymerase molecules or molecules to be detected (e.g., nucleic acid samples) may be attached for detection.

In some embodiments, one or more sensors 105 are designed to generate a radio-frequency (RF) voltage when excited under proper applied magnetic field and DC current bias. In one implementation, substantially all of the sensors 105 should oscillate at the same nominal frequency, where that frequency can be any value within a range of approximately 100 MHz-10 GHz. Here, the MNPs used for labeling nucleotide precursors or other molecules can be either ferromagnetic or superparamagnetic. An external magnetic field may be used to orient the magnetic moments of the all MNPs deposited into the array of STO-based sensors 105 in the same direction (nominally either parallel or antiparallel to the FM layers of the STO). The magnitude of this field should also be within a range in which the STOs can oscillate. As explained herein, when the MNPs are superparamagnetic, their presence can be detected by STO-based sensors 105 without the use of an applied magnetic field.

For any individual STO sensor 105 in the array, the presence of a MNP will generate an additional magnetic field local to that STO. Because the frequency of and noise in the RF signal generated by the STO is dependent upon the magnitude of the magnetic field acting upon the STO, its frequency can be shifted either up or down from what it would be in the absence of a MNP, and/or the phase noise of the RF signal can increase in the presence of a MNP. Therefore, a measurement of the STO signal frequency or detection/monitoring of the phase noise of the RF signal can be used to detect whether or not a MNP is present.

Detection Circuits

Determining the state of the sensor 105 (e.g., determining at what frequency the STO is oscillating, detecting the phase noise of an RF signal generated by the STO, etc.) can be accomplished using various types of detection circuitry.

Some embodiments use a delay line phase detector similar to those described in U.S. Pat. Nos. 8,654,465, 8,555,346, and 8,570,677, which describe detection circuits for reading data from magnetic media in a hard drive using a STO. U.S. Pat. Nos. 8,654,465, 8,555,346, and 8,570,677 are hereby incorporated by reference in their entireties for all purposes. Similar detectors can be used for molecule detection, namely to detect whether the frequency of a STO has shifted (e.g., due to presence or absence of a MNP).

Figure 7:
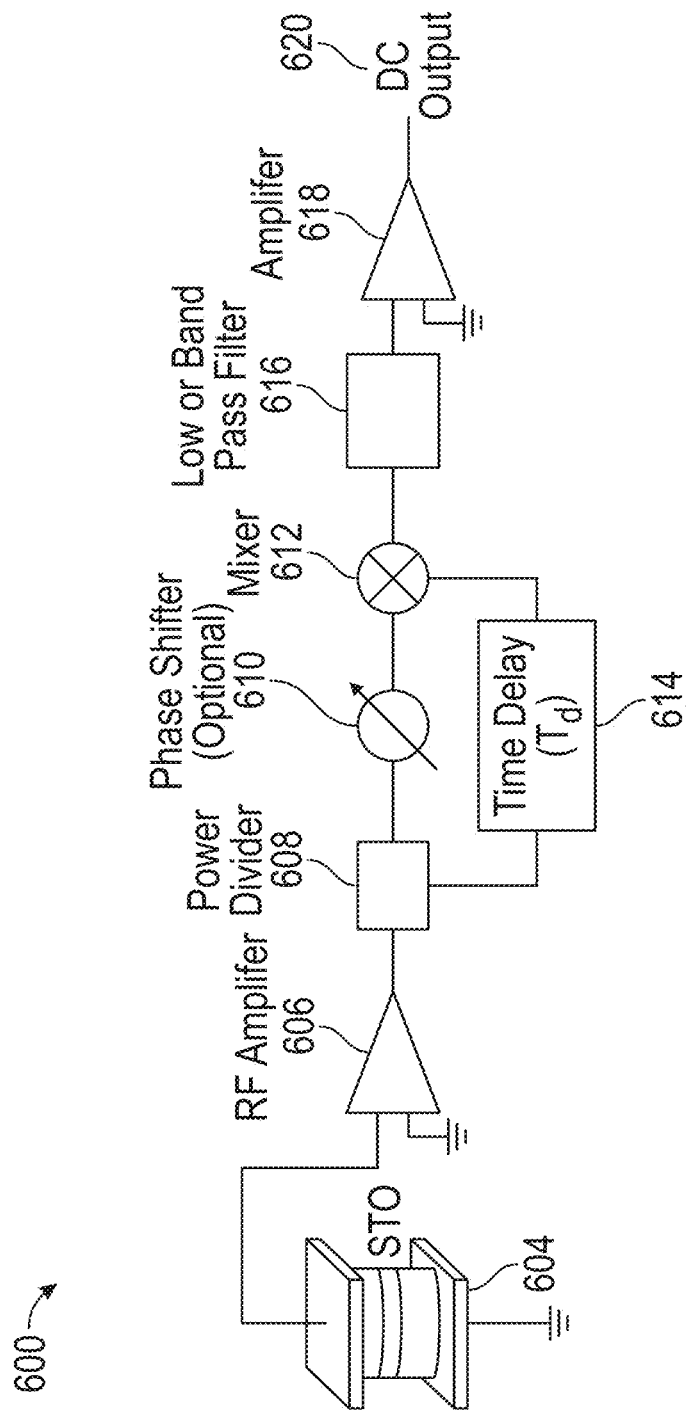
FIG. 7 illustrates a detection circuit in accordance with some embodiments.

FIG. 7 illustrates a delay line detection circuit 600 that can be used to measure the frequency of a RF signal in accordance with some embodiments. As illustrated in FIG. 7, the RF signal from the STO 604 is amplified by an RF amplifier 606 and split by a power divider 608 into two paths (e.g., two different lines). One path goes directly to an input of a mixer 612 (and thereby suffers a small, possibly negligible delay), while the other path adds an additional delay ($T_d$) 614 to the signal before sending the signal to the other input of the mixer 612. The time delay 614, which need not be large, can be introduced in any of several ways that will be appreciated by those having ordinary skill in the art. For example, the time delay 614 can be the result of routing one output of the power divider 608 through a longer wire trace than the other output of the power divider 608. Alternatively or in addition, other, more complicated approaches may be used.

As illustrated in FIG. 7, the output of the mixer 612 provides the input to a low or band pass filter 616. The output of the low or band pass filer 616 may be amplified by an optional amplifier 618, which provides a DC output 620 suitable for processing. The DC output 620 is proportional to the frequency of the RF signal generated by the STO 604.

To understand the operation of the delay line detection circuit 600, consider a signal V $\sin(2\pi ft+\varphi_1)$ output from the STO 604 where V, $f$, and $\varphi_1$ are the peak amplitude, frequency, and phase of the STO signal, respectively. Once the signal is split by the power divider 608, the delayed signal has a new phase at the mixer 612:

$$\varphi_2 = \varphi_1 + 2\pi f T_d$$

When the delayed signal is mixed with the original signal, the resulting mixer 612 output is:

$$v_{mix} = V\sin(2\pi ft+\varphi_1) \cdot V\sin(2\pi ft+\varphi_2) = V^2/2[\cos(2\pi(f-f)t+(\varphi_1-\varphi_2)) - \cos(2\pi(f+f)t+(\varphi_1+\varphi_2))].$$

The low or band pass filter 616 has a cutoff frequency selected so that it removes the second cosine term. Thus, because $\varphi_2 = \varphi_1 + 2\pi r f T_d$, the mixer 612 output simplifies to $$v_{mix} = \frac{V^2}{2}\cos(2\pi f T_d).$$

From this expression, one can see that the DC output 620 is dependent on the frequency of the signal from the STO 604 and the introduced time delay 614. If the time delay 614 is held constant, then the circuit 600 can be used to detect the STO 604 frequency by measuring or detecting the output voltage of the detection circuit 600 (DC output 620).

Unlike in magnetic recording, where the characteristic of interest is in the high frequency modulation of the STO frequency due to the fluctuating magnetic fields coming from bits on the magnetic media, the molecule detection (e.g., nucleic acid sequencing) applications contemplated by this disclosure would effectively be steady state because the chemistry cycles for introducing sequencing reagents typically are on the timescales of minutes and do not require real-time detection. Therefore, the mathematical model above is generally sufficient to describe the output of a detection circuit such as the detection circuit 600.

As shown in FIG. 7, an optional phase shifter 610 can be used to tune the phase difference between the signals on the two paths out of the power divider 608 to a value that results in the output signal (DC output 620) being approximately zero when the STO 604 is operating in its non-perturbed (i.e., without the presence of a MNP) state so that the detection circuit 600 operates in a linear region of phase/frequency. This approach allows for very rapid evaluation of the presence/absence of MNPs in a large area array of STOs 604, which could boost the bandwidth of the sequencing system and increase the speed of data collection.

One advantage of this detection approach is that if MNPs made of different ferromagnetic materials (and thus having different saturation magnetization Ms) are added to the fluidic channel(s) 115 of a detection device 100 (e.g., the nanofluidic or microfluidic channel(s) disposed near an array 110 of sensors 105) at the same time, they can be distinguished from one another because each type of MNP exerts a different, distinguishable magnetic field on a STO 604. Thus, each MNP type causes the STO 604 to generate a signal having a frequency that results in the DC output 620 allowing it to be distinguished from other MNP types in use. Therefore, if the STO/circuit signal-to-noise ratio (SNR) is large enough, the identification of the MNP type being detected by a STO 604 can be accomplished by reading the voltage at the output of the detection circuit 600 (DC output 620) and determining which MNP type is associated with the detected voltage level.

In DNA sequencing applications, for example, different MNP types can label each of the four different nucleotide precursors, thereby reducing the number of cycles per base read from two or four (which is currently done depending on the sequencing technology) to one. Because a cycle takes the order of minutes to complete, reducing the number of cycles required per base read would significantly improve the data collection throughput of a sequencing system.

For example, assume the DC output 620 of the detection circuit 600 varies as described above based at least in part on the type of MNP in the vicinity of a STO 604 in accordance with the following table:

| Magnetic nanoparticle identity | Nucleotide precursor labeled | Expected DC output | Base identity |
| --- | --- | --- | --- |
| MNP1 | A | $V_1 < v_{out} < V_2$ | T |
| MNP2 | C | $V_2 < v_{out} < V_3$ | G |
| MNP3 | T | $V_3 < v_{out} < V_4$ | A |
| MNP4 | G | $V_4 < v_{out} < V_5$ | C |

If the DC output 620 is detected to be in the range between $V_3$ and $V_4$, it can be determined that MNP3, which labels thymine, has been detected, meaning that the identity of the last-paired base is adenine.

Note that although FIG. 7 shows a single STO 604 at the input of the delay line detection circuit 600, an ensemble of STOs 604 could share a single detection circuit 600. In such embodiments, a multiplexer, switch, or similar device may be used to couple the STOs 604 to the detection circuit 600. Each STO 604 may then be read by cycling through the multiplexer, switch, etc. The use of a multiplexer or similar device to allow the detection circuit 600 to be shared may reduce the footprint of the detection circuitry 130 included in a detection device 100. It is also contemplated to use a separate circuit board or chip to implement the detection circuit 600 for a sequencing system; this approach could, however, increase the latency of the system.

Figure 8:
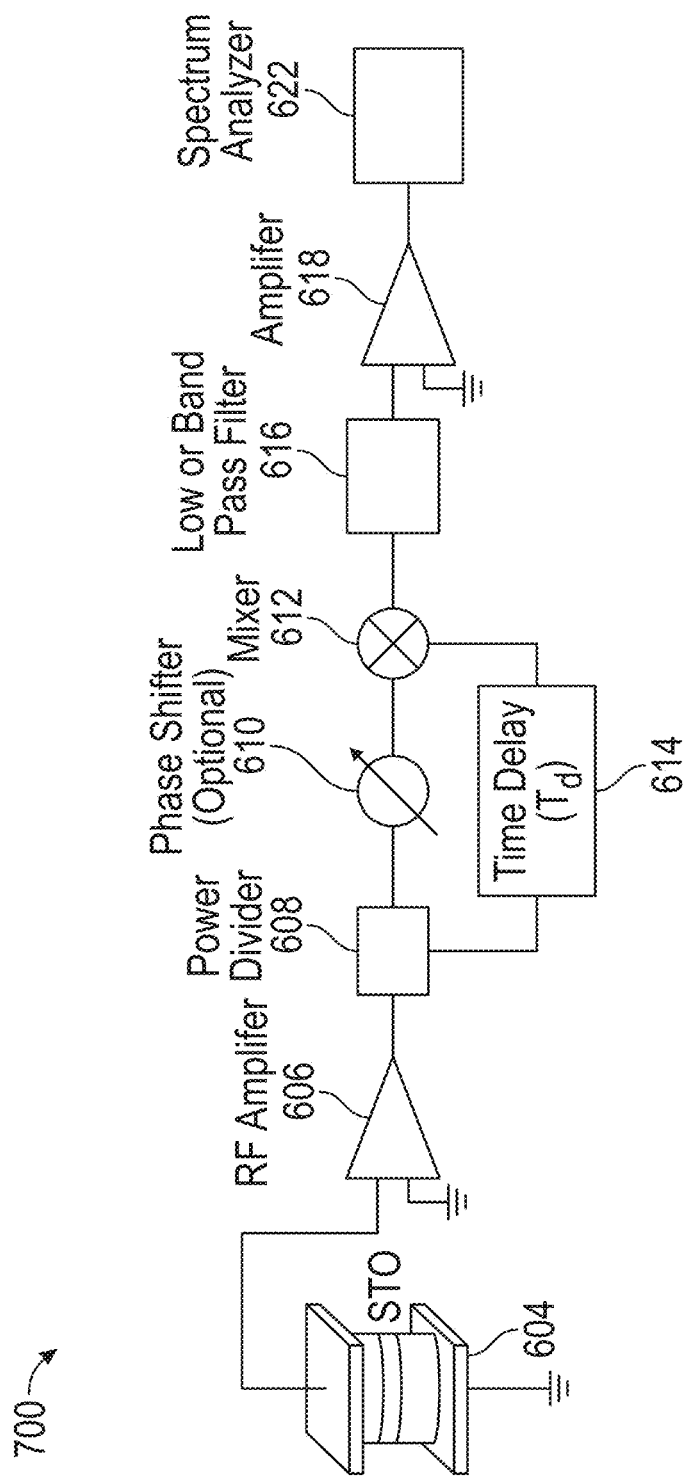
FIG. 8 illustrates a detection circuit in accordance with some embodiments.

Some embodiments use superparamagnetic MNPs (MNPs that are thermally unstable such that the magnetic field they generate fluctuates over time) as magnetic labels. In such embodiments, the fluctuating magnetic field from one or more thermally unstable MNPs in the vicinity of a STO 604 can increase the phase/frequency noise of the STO 604 without an external applied magnetic field. FIG. 8 illustrates a detection circuit 700 that can be used in accordance with some embodiments that use superparamagnetic MNPs. FIG. 8 illustrates many of the same components as discussed in the context of FIG. 7. The explanations of those components in the context of FIG. 7 apply as well for FIG. 8 and are not repeated here.

In FIG. 8, rather than the voltage of the output of the detection circuit (DC output 620 in FIG. 7) being analyzed directly to determine the frequency of the RF signal generated by the STO 604, the output signal is routed to a spectrum analyzer 622. Because the MNPs are superparamagnetic, the trace measured on the spectrum analyzer 622 is proportional to the spectral density of the combination of the intrinsic (thermal/magnetic) noise from the STO 604 and induced noise from the superparamagnetic MNPs. By integrating over the measured trace (e.g., measuring the area under the trace), an approximate value for the integrated phase/frequency noise of the STO 604 signal can be obtained. The presence of a MNP can be detected by comparing the measured integrated noise to that measured in a reference cell (in which a STO 604 is not exposed to a MNP).

Use of the detection circuit 700 of FIG. 8 may be advantageous because it does not require any equipment to generate a global magnetic field, but it may be slower than other approaches, such as, for example, using the detection circuit 600 of FIG. 7. The detection circuit 700 of FIG. 8 may use external spectrum analyzer electronics, which could increase cost and could be less convenient than other approaches. If used, however, an external spectrum analyzer 622 may be shared by multiple instances of detection circuits 700 (e.g., coupled to the spectrum analyzer 622 via a switch matrix, multiplexer, filter bank, etc.) to mitigate incremental cost. Alternative, the spectrum analyzer 622 functionality can be performed using a processer, such as a digital signal processor (DSP), that can be included in or used in addition to the detection circuitry 130.

Like the detection circuit 600 of FIG. 7, the detection circuit 700 of FIG. 8 may be shared by multiple STOs 604. For example, an ensemble of STOs 604 can be coupled to the detection circuit 700 via one or more multiplexers, switches, etc., which may reduce the footprint of the detection circuitry 130 on the detection device 100.

Figure 9:
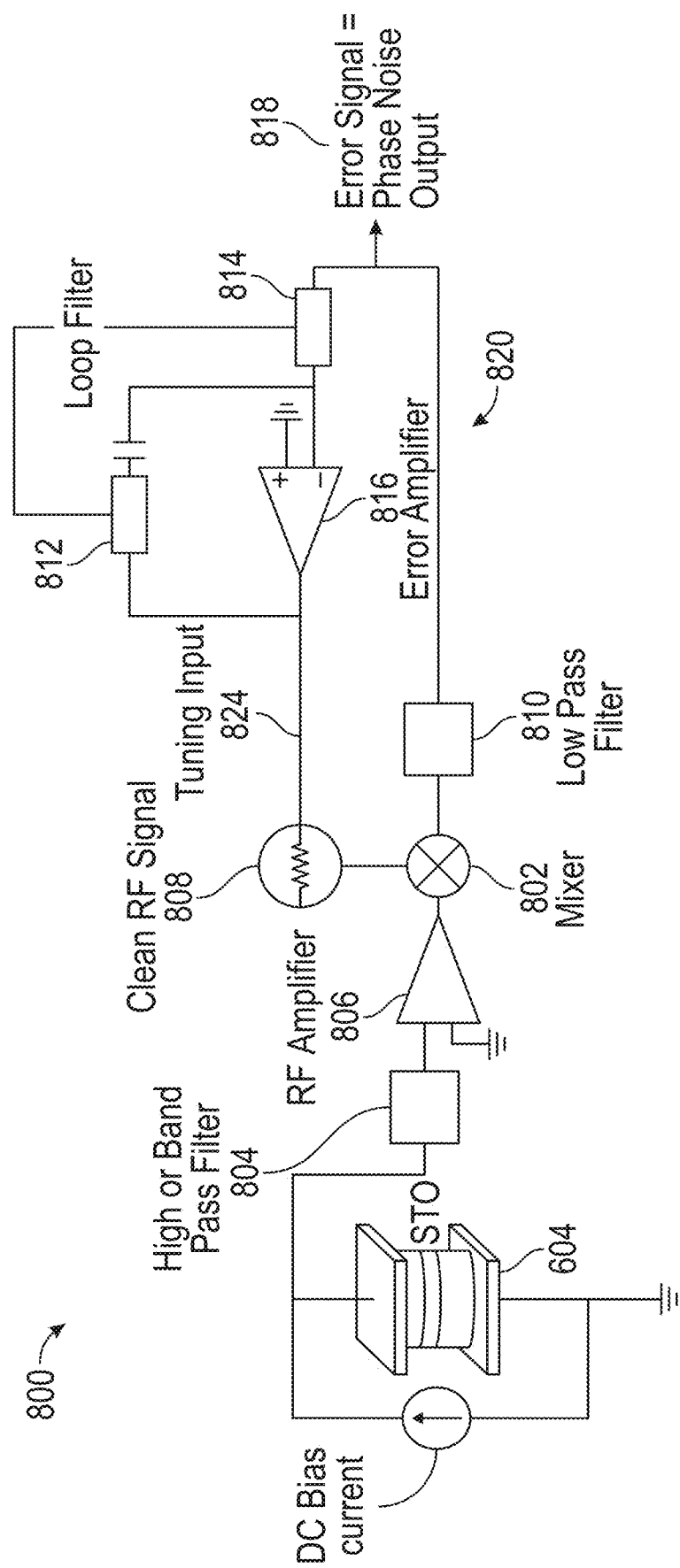
FIG. 9 illustrates a detection circuit in accordance with some embodiments.

FIG. 9 shows another detection circuit 800 in accordance with some embodiments. The detection circuit 800 allows the phase noise of the STO 604 to be measured directly (e.g., without using a spectrum analyzer 622). The frequency of the STO 604 is tracked by a phase locked loop (PLL) 820 with a low pass filter 810. The PLL 820 attempts to match the frequency of the RF signal generated by the STO 604, in which case the output signal from the PLL 820 is approximately zero. When the frequency of the RF signal shifts, the output of the PLL 820 becomes nonzero, which produces a nonzero error signal 818. Because the RF signal generated by a STO 604 will be noisier when there is a MNP (ferromagnetic or superparamagnetic) in its vicinity when there is no MNP in its vicinity, the detection circuit 800 detects the phase/frequency noise in the RF signal generated by the STO 604.

The detection circuit 800 includes many of the same elements as the detection circuits 600 and 700 shown in FIGS. 7 and 8, respectively, and the descriptions of those elements are not repeated here. In the exemplary embodiment of FIG. 9, the PLL 820 includes a signal generator 808, which generates a clean RF signal based on a tuning input 824. The tuning input 824 is determined by a loop filter that includes components 812 and 814 (which may be resistors) and an error amplifier 816. A mixer 802 mixes the clean RF signal from the signal generator 808 with the signal output from the amplifier 806. A low pass filter 810 of the PLL 820 then filters the output from the mixer 802. The resultant error signal 818 output from the PLL 820 is the phase noise of the STO 604, the characteristics of which depend on (e.g., are influenced or changed by) the presence or absence of a MNP. Thus, the error signal 818 can be used to detect the presence or absence of one or more MNPs in the vicinity of the STO 604.

Detection Methods

The sensors 105 and/or detection devices 100 described above may be used to detect molecules labeled by MNPs, as described further below. Suitable detection methods include those in which a binary decision (e.g., yes/no, 1/0, etc.) is made as to whether a MNP, and therefore a molecule to which the MNP is coupled, is present in the vicinity of a sensor 105. For simplicity, the explanation below is presented in the context of DNA sequencing, but, as stated previously, it is to be understood that the methods described also may be used in other applications and to detect types of molecules other than nucleic acids.

In some embodiments, target molecules to be detected (e.g., nucleic acid strands to be sequenced) are attached to the walls 117 of the fluidic channel(s) 115 of a detection device 100. Polymerase may be introduced at this point. For example, the polymerase may be bound (attached or coupled) to the wall 117 along with a target ssDNA to be sequenced. Nucleotide precursors labeled by MNPs may then be introduced into the fluidic channel(s) 115. The polymerase operates to incorporate complementary nucleotide precursors labeled by MNPs into the target DNA strand. Only the appropriate (complementary) base (i.e., for DNA sequencing, cytosine (C) with guanine (G) or adenine (A) with thymine (T)) will be incorporated, and its presence can be detected by the sensors 105. Assuming this process is done one base pair at a time, the presence or absence of the MNP labeling the complementary nucleotide precursor, and therefore the identity of base with which that nucleotide precursor pairs in the target DNA strand, can be determined using the various device embodiments of, for example, FIGS. 4A-9.

The presence or absence of a MNP in the vicinity of a particular sensor 105 can be detected, for example, by applying a magnetic field across the sensor 105 and applying a bias current to read the sensor 105. The application of a magnetic field across the sensor 105 is optional (for example, as explained above, the detection circuit 700 illustrated in FIG. 8 may be used without application of a magnetic field), but it may be beneficial in applications in which multiple types of MNPs are present (e.g., in DNA sequencing applications in which different nucleotide precursors are labeled by different MNP types and multiple nucleotide precursors are added to the fluidic channel 115 at substantially the same time). If applied, the magnetic field may be applied using an electromagnet, e.g., by placing the pole pieces on either side of the detection device), a distributed coil, a solenoid oriented perpendicular to the fluidic channel 115, etc. to generate the magnetic field in the direction of the pinned layer 314's moment. The means for generating the magnetic field may be mounted, for example, on the bottom surface 119 of the detection device 100. As another example, the means for generating a magnetic field may be included in a system that includes the detection device 100. It is to be understood that other suitable means of generating the magnetic field, such as, for example, by using permanent magnets or super-conducting magnets, are possible, are specifically contemplated herein, and are not excluded. If used, the applied magnetic field aligns the moments of all of the MNPs in a common direction so that the measured signals due to the presence of a MNP are similar.

With the free layer excited through spin transfer effects and the fixed layer with its moment fixed, a STO excited as described above (e.g., in the context of FIG. 3C) will produce a RF voltage signal from an applied DC current due to resistance fluctuations caused by magnetoresistive effects. Therefore, by connecting the sensors 105 to detection electronics/circuitry as described above, the presence and/or absence of MNPs near the sensors 105 can be detected. In DNA sequencing applications, for example, nucleotide precursors (or, more generally, nucleic acids) labeled by MNPs and incorporated into a target DNA strand by polymerase may be detected by determining the frequency or frequency noise of the RF signal generated by a STO, because only in the presence of a MNP labeling the nucleotide precursor incorporated in a target DNA strand being sequenced would the local magnetic field be sufficient to shift the oscillation frequency of or increase the noise in a RF signal generated by the STO.

Figure 10:
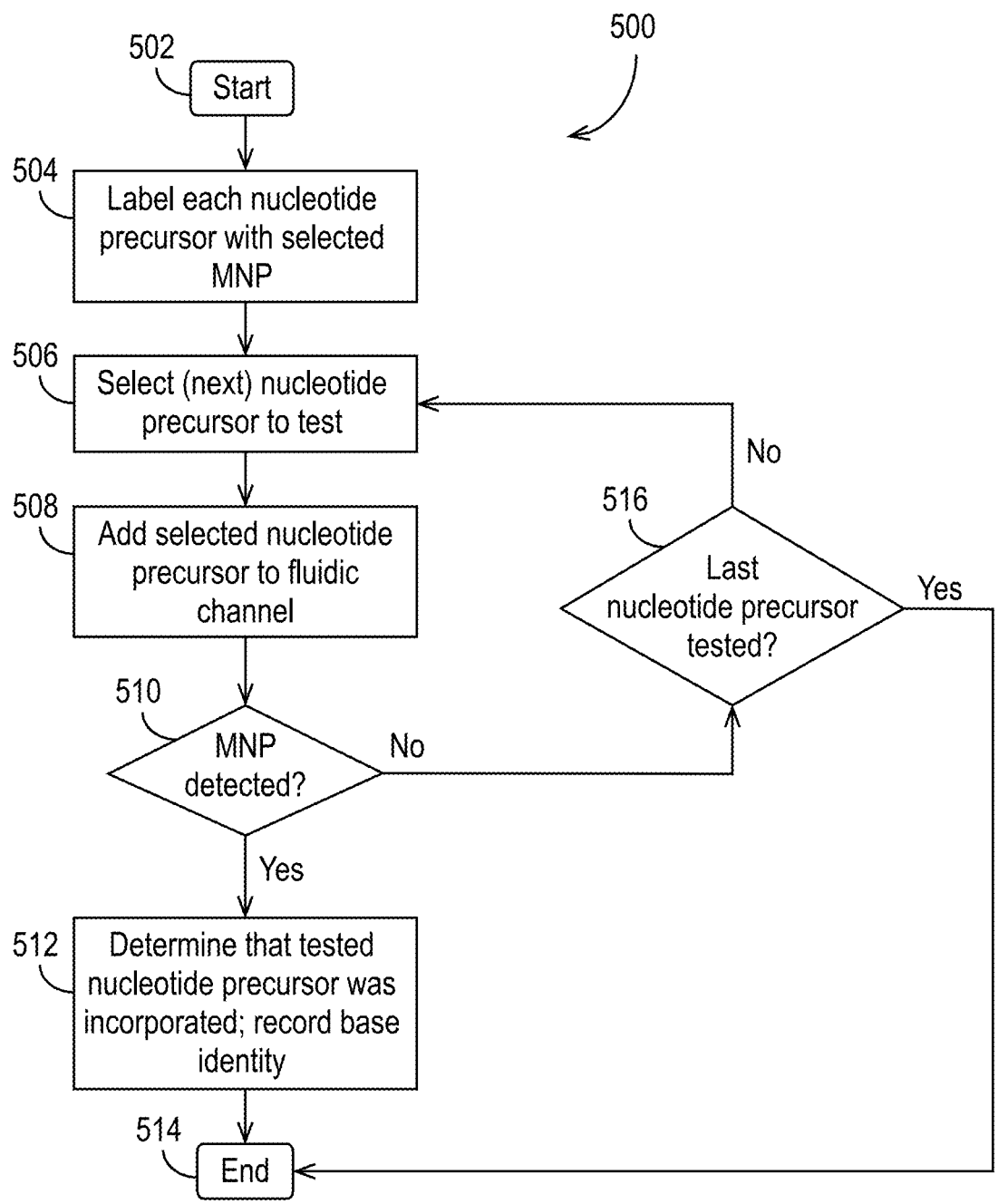
FIG. 10 illustrates an exemplary sequential binary method suitable for DNA sequencing in which a single MNP type is used to label multiple nucleotide precursors in accordance with some embodiments.

Methods of molecule detection may use a single MNP type or multiple MNP types. FIG. 10 illustrates an exemplary sequential binary method 500 suitable for DNA sequencing in which a single MNP type is used to label all four nucleotide precursors in accordance with some embodiments. It is to be understood that FIG. 10 illustrates the procedure for a single sensor 105. In embodiments in which a detection device 100 includes a plurality of sensors 105, some of the steps of the method 500 (e.g., steps 510, 512, 516) may be performed independently for each of the plurality of sensors 105.

At 502, the method 500 begins. At 504, molecules of each of the four nucleotide precursors (A, T, C, and G) are all labeled by the same type of MNP. The different nucleotide precursors, each labeled by the same MNP type, are then introduced one at a time into, for example, a fluidic channel 115 of a detection device 100. Thus, at 506, a first nucleotide precursor to be tested is selected. At 508, the selected (magnetically-labeled) nucleotide precursor is added to the fluidic channel 115 of a detection device 100. After sufficient time has passed to allow the nucleotide precursor to be incorporated in the target DNA strands being sequenced, at 510, detection circuitry 130 detects whether a MNP is present in the vicinity of a STO 604.

Step 510 can be accomplished in a number of ways. For example, in embodiments using the detection circuit 600 of FIG. 7 (or a similar circuit), the presence of a MNP can be presumed when the DC output 620 exceeds a threshold. As another example, in embodiments using the detection circuit 700 of FIG. 8 (or a similar circuit) and superparamagnetic MNPs, the presence of a MNP can be presumed when the spectrum analyzer 622 detects that the STO 604 is generating a RF signal having a phase noise that exceeds a threshold. As yet another example, in an embodiment using the detection circuit 800 of FIG. 9 (or a similar circuit), the presence of a MNP (which can be, but is not required to be, superparamagnetic) can be presumed when the error signal 818 exceeds a threshold.

If it is determined at 510 that a MNP is present in the vicinity of a STO, then at 512 it is determined that the tested nucleotide precursor was incorporated into a DNA strand coupled to a binding site associated with the sensor 105. The identity of the base with which the tested nucleotide precursor paired (its complement) may then be recorded, and the method ends at 514. If, however, is it determined at 510 that a MNP not present in the vicinity of the STO (interpreted to mean that the previously-tested nucleotide precursor was not incorporated at the binding site(s) associated with the sensor 105), then at 516 it is determined whether the previously-tested nucleotide precursor was the last of the four nucleotide precursors to be tested. If so, then the method ends at 514. If not, the method returns to 506, where the next nucleotide precursor to be tested is selected, and at least steps 508 and 510 are repeated. Once the method 500 has ended, the magnetic label may be cleaved prior to beginning the next sequencing cycle.

The method 500 can be performed using one or more sensors 105. It is to be appreciated that when more than one sensor 105 is used, the decision at 510 can differ for different sensors 105. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, non-overlapping sub-strands (e.g., ATGG and TTAG) as well as, if a plurality of the longer strands are cut into sub-strands, sub-strands that partially or completely overlap other sub-strands (e.g., GGCTTA and TTAG). All of the smaller, randomized sub-strands may be sequenced at the same time, potentially after being amplified. In such applications, it will be appreciated that because the sub-strands do not represent the same sub-sequences, it may be desirable to detect RF signals generated by each sensor 105 to detect MNPs because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it is desirable, in each sequencing cycle, to determine whether and at which physical location(s) each dNTP type has been incorporated. Accordingly, when using the exemplary method 500 shown in FIG. 10, the decision at 510 may be "yes" for one sensor 105 after addition of a particular nucleotide precursor and "no" for another. Thus, when sequencing randomized sub-strands of a nucleic acid such as DNA, it may be desirable to test all four nucleotide precursors during each sequencing cycle, even though for some of the sensors 105 the decision at 510 is "yes" for the first, second, or third tested nucleotide precursor.

Although FIG. 10 assumes that each of the nucleotide precursors is labeled by the same type of MNP, it is not a requirement to use the same type of MNP for each of the nucleotide precursors. For example, it may be convenient to use the same type of MNP for each of the nucleotide precursors, but, alternatively, different nucleotide precursors may be labeled by different types of MNP. In other words, two or more of the nucleotide precursors may be labeled by the same type of MNP, or two or more nucleotide precursors may be labeled by different types of MNP.

For example, various other embodiments are directed to using multiple MNP types (for example, MNP 1, 2, 3, and 4), each causing the sensor 105 to generate a RF signal with properties distinguishing it from other RF signals caused by the other three MNP types. Focusing on the DNA example for illustration, each individual base (A, T, C, G) can be labeled by a different type of MNP (e.g., base A with MNP 1, base C with MNP 2, base G with MNP 3, and base T with MNP 4) by either labeling each base separately and mixing them together or functionalizing each type of MNP differently so that it has an affinity for a particular (e.g., its assigned) base. In a single chemistry run, all tagged (magnetically-labeled) bases may be introduced into a microfluidic cell (e.g., the fluidic channel 115 of the detection device 100) in which DNA strands (e.g., fragments) to be sequenced have been attached within the microfluidic cell (e.g., as described in the discussion above of the detection devices 100).

After binding the target DNA strands to be sequenced to the detection device 100, all four magnetically-labeled nucleotide precursors can be introduced into the fluidic channel at the same time (or substantially the same time). Polymerase acts to incorporate nucleotide precursors that are complementary to those in the target strand. RF signals generated (or not generated) by STOs of the detection device 100 can be used to identify which MNP (and, therefore, nucleotide precursor), if any, has been incorporated in the vicinity of each sensor 105. After each nucleotide precursor has been introduced in the fluidic channel(s) 115, and the sensors 105 have been read, the MNPs may be cleaved from the incorporated magnetically-labeled nucleotide precursor using, for example, enzymatic or chemical cleavage, as is known in the art. The process can then be repeated for the next unpaired base in the strand being sequenced.

Accordingly, in some embodiments for DNA sequencing applications, instead of using a binary method with four chemistry steps for each base read (sequencing cycle), four different MNPs, each causing the STO to generate a distinguishable RF signal or distinguishable changes in RF signals, can be used as the magnetic labels, and all of them can be detected in a single chemistry step. For example, each type of molecule (e.g., in DNA sequencing applications, each dNTP type) can be labeled by a different MNP type, where each MNP type causes the STO to generate (or not generate) a RF signal having at least one characteristic (e.g., frequency, frequency noise) enabling the presence or absence of the MNP to be distinguished from all other MNPs being used as magnetic labels. For example, in a DNA sequencing application, A can be labeled by MNP1, T by MNP2, C by MNP3, and G by MNP4, where the RF signals generated by STOs influenced by MNP1, MNP2, MNP3, and MNP4 are distinguishable by the detection circuitry 130. Detection circuitry 130 (e.g., the exemplary embodiments shown and described in the context of FIGS. 7-9) can identify which of the nucleotide precursors has been incorporated into the DNA strand bound in the vicinity of and associated with each STO.

For example, as explained above (see, e.g., the discussion of FIG. 7), the DC output 620 of the detection circuit 600 may be at different levels that depend on the MNP type in the vicinity of a STO 604. Thus, using a table or key as described above, a detected DC output 620 voltage can be mapped to one of the four MNP types.

Figure 11:
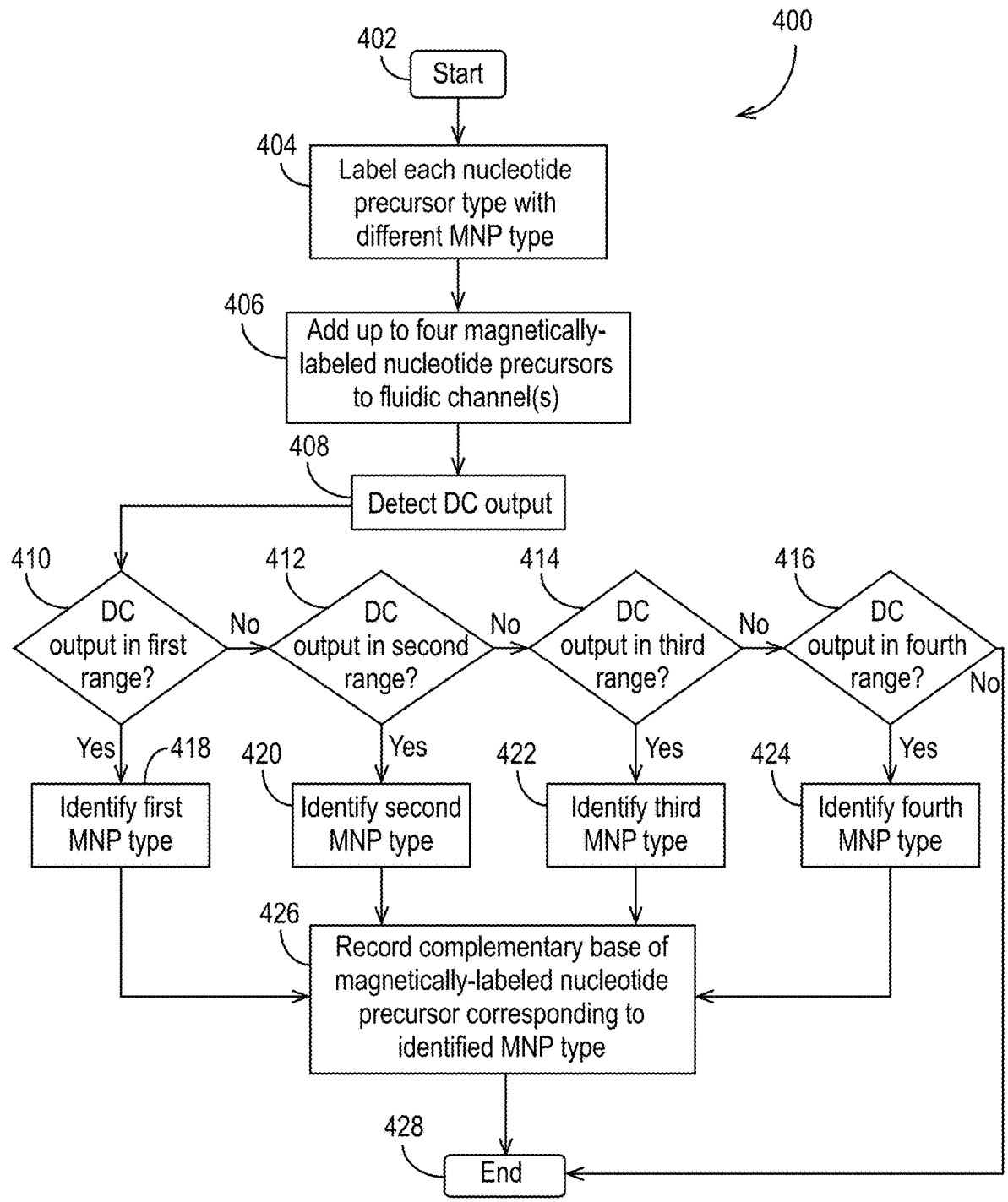
FIG. 11 is a flowchart illustrating a method suitable for DNA sequencing using multiple nucleotide precursors labeled by different MNP types in accordance with some embodiments.

FIG. 11 is a flowchart illustrating a method 400 suitable for DNA sequencing using multiple nucleotide precursors labeled by different MNP types and detection circuitry 130 including the detection circuit 600 shown in FIG. 7 (or a similar circuit) in accordance with some embodiments. FIG. 11 assumes that all four nucleotide precursors are labeled by different MNP types that allow them to be distinguished, and that all four magnetically-labeled nucleotide precursors are added to the fluidic channel 115 at substantially the same time, but it is to be appreciated that the method 400 can be performed with fewer nucleotide precursors being labeled by distinguishable MNPs and/or introduced into the fluidic channel 115 at substantially the same time.

At 402, the method 400 begins. At 404, molecules of each the four nucleotide precursors (A, T, C, and G) are labeled by a different type of MNP. At 406, up to all of the different nucleotide precursors, each labeled by a different MNP type, are then introduced at substantially the same time into, for example, a fluidic channel 115 of a detection device 100. After sufficient time has passed to allow the magnetically-labeled nucleotide precursors to be incorporated in the target DNA strands being sequenced, at 408, detection circuitry 130 detects a DC output from the detection circuit (e.g., DC output 622 from detection circuit 600).

Next, it is determined which one of the four MNP types is most likely to be responsible for the detected DC output. FIG. 11 illustrates one way to make the determination. In FIG. 11, at 410, it is determined whether the DC output is in a first range of values, where the first range of values corresponds to the first MNP type. If so, then at 418, the first MNP type is identified as being the MNP type detected, and, at 426, the identity of the base that is complementary to the nucleotide precursor labeled by the first MNP type is recorded, and the method 400 ends at 428 for the sensor 105. If it is determined at 410 that the DC output is not in the first range of values, then at 412, it is determined whether the DC output is in a second range of values, where the second range of values corresponds to the second MNP type. If so, then at 420, the second MNP type is identified as being the MNP type detected, and, at 426, the identity of the base that is complementary to the nucleotide precursor labeled by the second MNP type is recorded, and the method 400 ends at 428 for the sensor 105. If it is determined at 412 that the DC output is not in the second range of values, then at 414, it is determined whether the DC output is in a third range of values, where the third range of values corresponds to the third MNP type. If so, then at 422, the third MNP type is identified as being the MNP type detected, and, at 426, the identity of the base that is complementary to the nucleotide precursor labeled by the third MNP type is recorded, and the method 400 ends at 428 for the sensor 105. If it is determined at 414 that the DC output is not in the third range of values, then at 416, it is determined whether the DC output is in a fourth range of values, where the fourth range of values corresponds to the fourth MNP type. If so, then at 424, the fourth MNP type is identified as being the MNP type detected, and, at 426, the identity of the base that is complementary to the nucleotide precursor labeled by the fourth MNP type is recorded. If not, then the method 400 (and the sequencing cycle) ends at 428 without identification of any MNP type.

It is to be appreciated that FIG. 11 is only one way detection can be performed using a detection circuit like the one illustrated in FIG. 7. Moreover, the steps illustrated in FIG. 11 can be altered. For example, although FIG. 11 shows the steps 410, 412, 414, and 416 as being performed sequentially, they could be performed in parallel. Furthermore, as will be appreciated, once the DC output has been detected, a look-up table could be used to determine which of the MNP types has been detected (if any). There are other ways that FIG. 11 can be modified that will be apparent in light of the disclosures herein. Accordingly, FIG. 11 is merely exemplary and is not intended to be limiting.

Additionally, as explained above in the context of FIG. 10, the method 400 can be performed using one or more sensors 105. It is to be appreciated that when more than one sensor 105 is used, the decisions at different decision points (e.g., 410, 412, 414, 416) can differ for different sensors 105.

After the method 400 ends, the MNPs may be cleaved from the incorporated magnetically-labeled nucleotide precursor using, for example, enzymatic or chemical cleavage, as is known in the art. The method 400 can then be repeated to identify the next unpaired base in the strand being sequenced.

In embodiments using superparamagnetic MNPs and a detection circuit 700 as illustrated in FIG. 8, the frequency noise of the RF signal generated by a STO 604 may be measured/detected directly, and without an applied magnetic field, to detect molecules. As long as each MNP type in use causes the STO 604 to generate a RF signal having a frequency noise that is distinguishable from the frequency noises of the RF signals generated by the STO 604 in the presence of each of the other types of MNP, the identity of the MNP, and therefore the last-paired base, can be determined from the detected frequency noise of the RF signal generated by the MNP.

Figure 12:
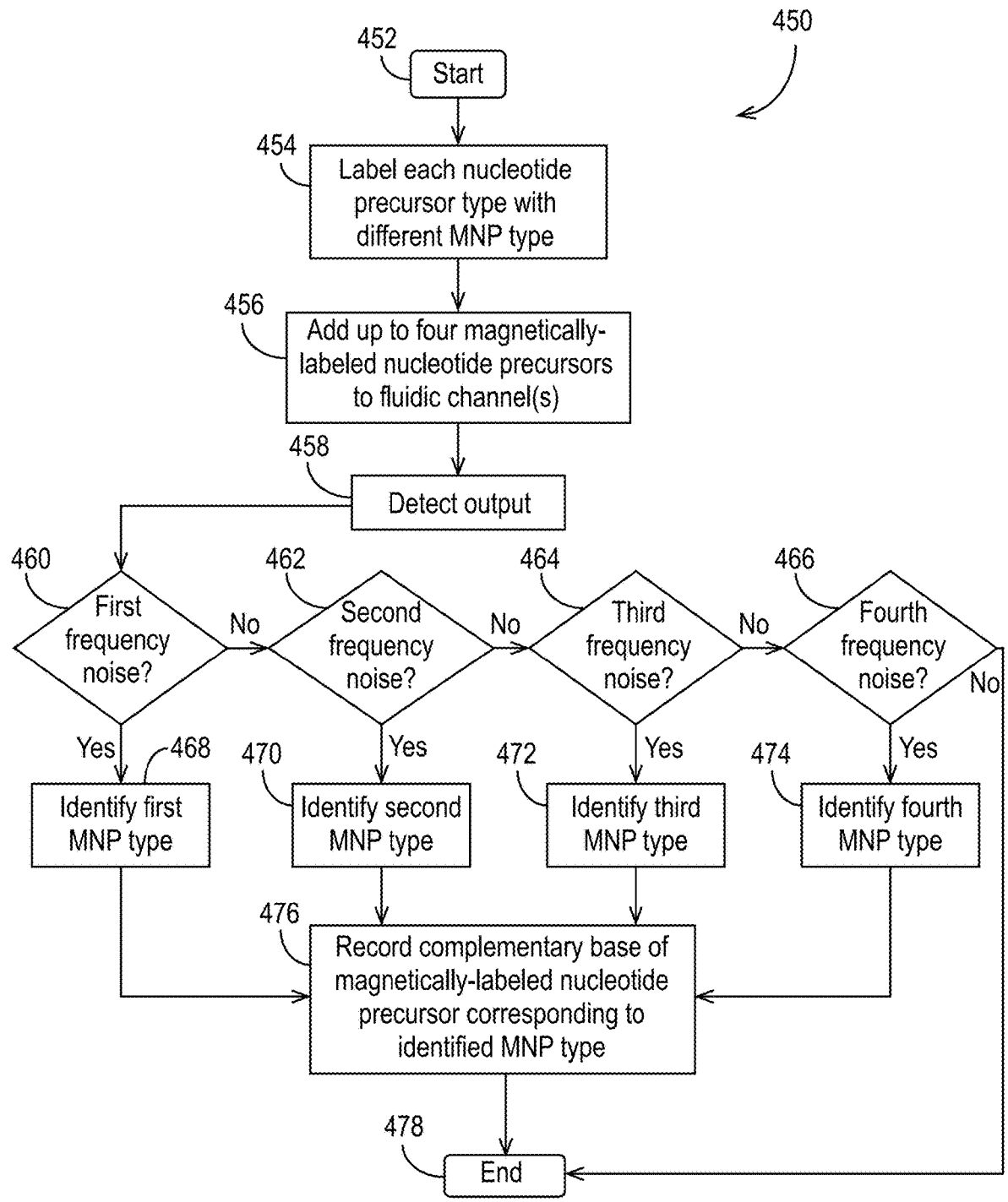
FIG. 12 is a flowchart illustrating another method suitable for DNA sequencing using multiple nucleotide precursors labeled by different MNP types in accordance with some embodiments.

FIG. 12 is a flowchart illustrating a method 450 suitable for DNA sequencing using multiple nucleotide precursors labeled by different (e.g., superparamagnetic) MNP types and detection circuitry 130 including the detection circuit 700 shown in FIG. 8 (or a similar circuit) in accordance with some embodiments. FIG. 12 assumes that all four nucleotide precursors are labeled by different MNP types that allow them to be distinguished, and that all four magnetically-labeled nucleotide precursors are added to the fluidic channel 115 at substantially the same time, but it is to be appreciated that the method 450 can be performed with fewer nucleotide precursors being labeled by distinguishable MNPs and/or introduced into the fluidic channel 115 at substantially the same time.

At 452, the method 450 begins. At 454, molecules of each the four nucleotide precursors (A, T, C, and G) is labeled by a different type of MNP. As explained above, the MNPs may be superparamagnetic, which allows their detection without an applied magnetic field. At 456, up to all of the different nucleotide precursors, each labeled by a different MNP type, are then introduced at substantially the same time into, for example, a fluidic channel 115 of a detection device 100. After sufficient time has passed to allow the magnetically-labeled nucleotide precursors to be incorporated in the target DNA strands being sequenced, at 458, detection circuitry 130 detects a frequency noise of the signal generated by the sensor 105 (e.g., using a spectrum analyzer as illustrated in detection circuit 700).

Next, one of the four MNP types is identified based on the detected frequency noise. In FIG. 12, at 460, it is determined whether the detected frequency noise is a first frequency noise that corresponds to the first MNP type. This determination can be done in any of a number of ways. For example, as described above in the discussion of FIG. 8, the spectral density of the combination of the intrinsic (thermal/magnetic) noise from the STO 604 and induced noise from the superparamagnetic MNPs (e.g., without application of a magnetic field) can be determined to determine if the frequency noise indicates the presence of one or more MNPs. If so, then at 468, the first MNP type is identified as being the MNP type detected, and, at 476, the identity of the base that is complementary to the nucleotide precursor labeled by the first MNP type is recorded, and the method 450 ends for the sensor 105 at 478. If the detected frequency noise is not the first frequency noise, then at 462, it is determined whether the detected frequency noise is a second frequency noise that corresponds to the second MNP type. If so, then at 470, the second MNP type is identified as being the MNP type detected, and, at 476, the identity of the base that is complementary to the nucleotide precursor labeled by the second MNP type is recorded, and the method 450 ends for the sensor 105 at 478. If the detected frequency noise is not the second frequency noise, then at 464, it is determined whether the detected frequency noise is a third frequency noise that corresponds to the third MNP type. If so, then at 472, the third MNP type is identified as being the MNP type detected, and, at 476, the identity of the base that is complementary to the nucleotide precursor labeled by the third MNP type is recorded, and the method 450 ends for the sensor 105 at 478. If the detected frequency noise is not the third frequency noise, then at 466, it is determined whether the detected frequency noise is a fourth frequency noise that corresponds to the fourth MNP type. If so, then at 474, the fourth MNP type is identified as being the MNP type detected, and, at 476, the identity of the base that is complementary to the nucleotide precursor labeled by the fourth MNP type is recorded, and the method 450 ends for the sensor 105 at 478. If not, then the cycle ends at 478 without identification of any MNP type for the sensor 105.

It is to be appreciated that FIG. 12 is only one way detection can be performed using a detection circuit like the one illustrated in FIG. 8. Moreover, the steps illustrated in FIG. 12 can be altered. For example, although FIG. 12 shows the steps 460, 462, 464, and 466 as being performed sequentially, they could be performed in parallel. Furthermore, as will be appreciated, once the frequency noise of the RF signal generated by the STO 604 has been detected, a look-up table could be used to determine which of the MNP types has been detected (if any).

Accordingly, FIG. 12 is merely exemplary and is not intended to be limiting.

Additionally, as explained above in the context of FIG. 10, the method 450 can be performed using one or more sensors 105. It is to be appreciated that when more than one sensor 105 is used, the decisions at different decision points (e.g., 460, 462, 464, 466) can differ for different sensors 105.

The detection circuit 800 shown in FIG. 9 can also be used in embodiments in which different nucleotide precursors are labeled by different types of MNP and multiple nucleotide precursors are introduced in to the fluidic channel 115 at substantially the same time. For example, the detection circuit 800 can include a tunable reference oscillator (signal generator 808) to generate the clean RF signal described above in the discussion of FIG. 9. Optionally, other portions of the detection circuit 800 can be adaptive or tunable (e.g., the loop filter 820 can be adaptive or modifiable). During each sequencing cycle, after allowing sufficient time for incorporation, the frequency of the clean RF signal can be set, in turn, to the frequency the RF signal generated by the STO 604 is expected to have in the presence of each MNP type in use. By monitoring whether the error signal 818 exceeds a threshold for each of the tested frequencies, thereby detecting the "noisiness" of the RF signal at the expected frequency, the detection circuitry 130 can determine which, if any, of the MNP types is in the vicinity of the STO 604.

Figure 13:
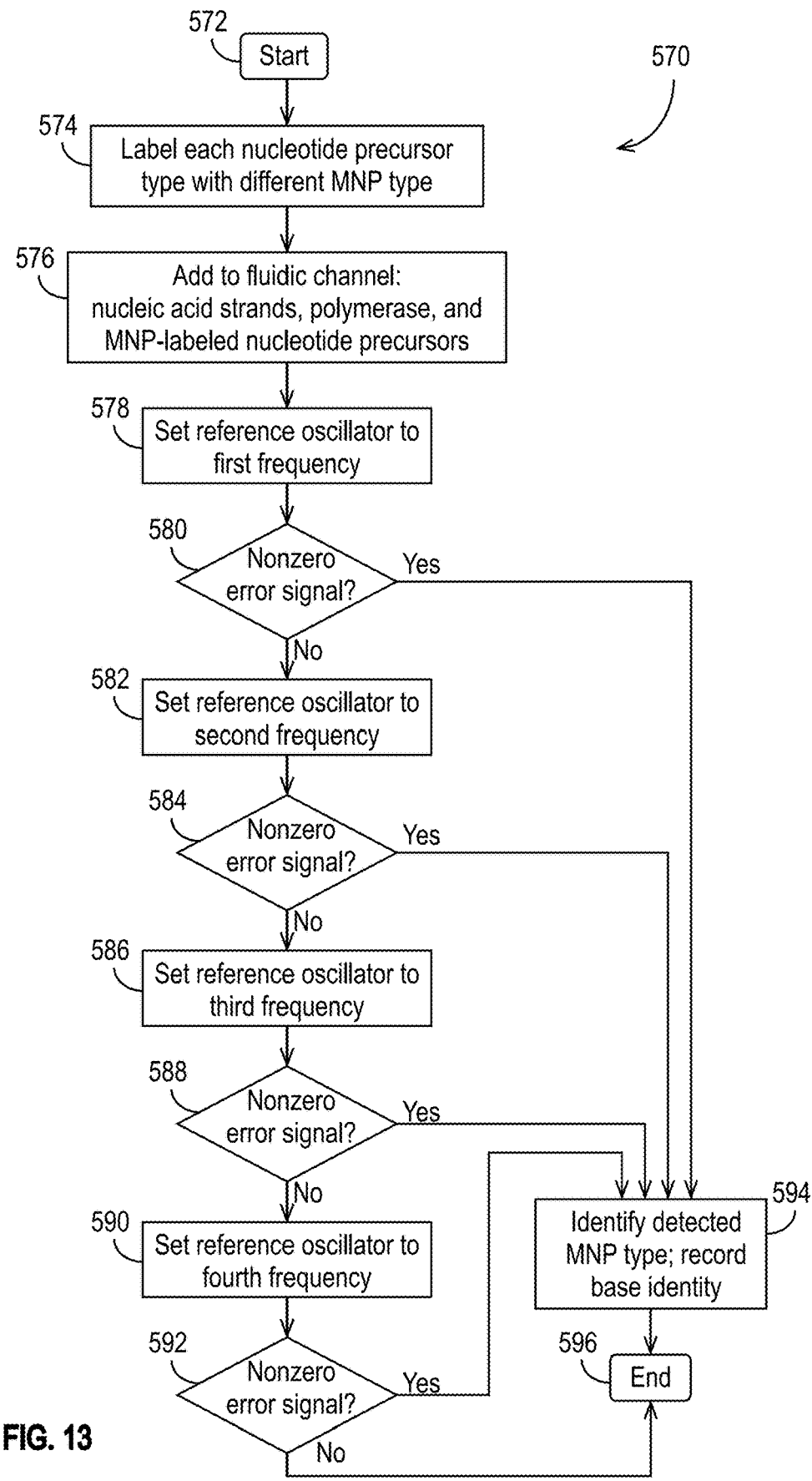
FIG. 13 illustrates a method suitable for DNA sequencing using MNP-labeled nucleotide precursors and a tunable reference oscillator in accordance with some embodiments.

FIG. 13 illustrates a method 570 suitable for DNA sequencing using MNP-labeled nucleotide precursors and a tunable reference oscillator 808 in accordance with some embodiments. At 572, the method 570 begins. At 574, each nucleotide precursor type (G, A, C, T) is labeled by a different MNP type (e.g., A by MNP1, T by MNP2, C by MNP3, and G by MNP4). At 576, nucleic acid strands to be sequenced, polymerase molecules, and the MNP-labeled nucleotide precursors are introduced in to the fluidic channel 115 of a detection device 100. After a period of time suitable to allow incorporation of the nucleotide precursors, at 578, the reference oscillator is set to generate a RF signal at first frequency, where the first frequency is the expected oscillation frequency of the RF signal generated by the STO 604 in the presence of the first MNP type. At 580, the detection circuitry 130 (e.g., detection circuit 800) determines whether an error signal is nonzero (e.g., whether it is greater than a threshold). If so, then it can be inferred at 594 that the STO 604 has detected the first MNP type, the identity of the complementary base can be recorded, and the method 570 ends for the sensor 105 at 596. If not, then the method 570 proceeds to 582, and the reference oscillator is set to generate a RF signal at second frequency, where the second frequency is the expected oscillation frequency of the RF signal generated by the STO 604 in the presence of the second MNP type. At 584, the detection circuitry determines whether an error signal is nonzero (e.g., whether it is greater than a threshold). If so, then it can be inferred at 594 that the STO 604 has detected the second MNP type, the identity of the complementary base can be recorded, and the method 570 ends for the sensor 105 at 596. If not, then the method 570 proceeds to 586, and the reference oscillator is set to generate a RF signal at third frequency, where the third frequency is the expected oscillation frequency of the RF signal generated by the STO 604 in the presence of the third MNP type. At 588, the detection circuitry determines whether an error signal is nonzero (e.g., whether it is greater than a threshold). If so, then it can be inferred at 594 that the STO 604 has detected the third MNP type, the identity of the complementary base can be recorded, and the method 570 ends for the sensor 105 at 596. If not, then the method 570 proceeds to 590, and the reference oscillator is set to generate a RF signal at fourth frequency, where the fourth frequency is the expected oscillation frequency of the RF signal generated by the STO 604 in the presence of the fourth MNP type. At 592, the detection circuitry determines whether an error signal is nonzero (e.g., whether it is greater than a threshold). If so, then it can be inferred at 594 that the STO 604 has detected the fourth MNP type, the identity of the complementary base can be recorded, and the method 570 ends for the sensor 105 at 596. If not, then the method ends for the sensor 105 at 596 without the detection of any MNP in the vicinity of the STO 604.

It is to be appreciated that the detection circuitry 130 may include a plurality of reference oscillators 808, each configured to generate a frequency that is close to the frequency of the STO's RF signal in the presence of one of the MNP types being used. During each sequencing cycle, after the four MNP-labeled nucleotide precursors are introduced, a switch may cycle through each reference oscillator 808 in turn, and the error signal may be detected as described above. Once again, the error signal should be nonzero only when the switch is connected to the reference oscillator 808 that is oscillating at approximately the oscillation frequency of the STO in the presence of the MNP type associated with that frequency. From this information, the identity of the particle can be determined.

Methods of Fabricating Sensors and Detection Devices

Figure 14A:
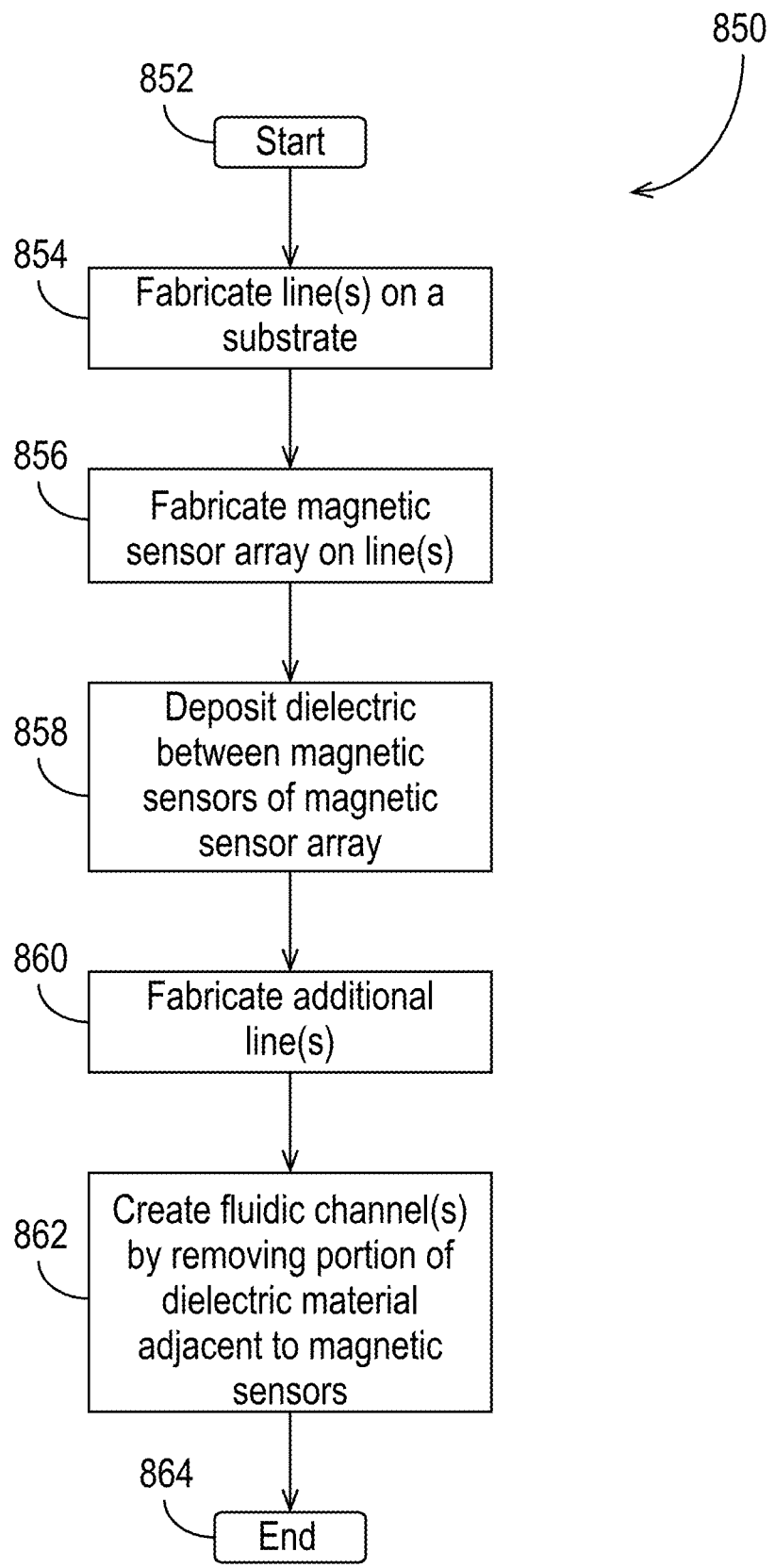
FIG. 14A illustrates a method of manufacturing the detection device in accordance with some embodiments.
Figure 14B:
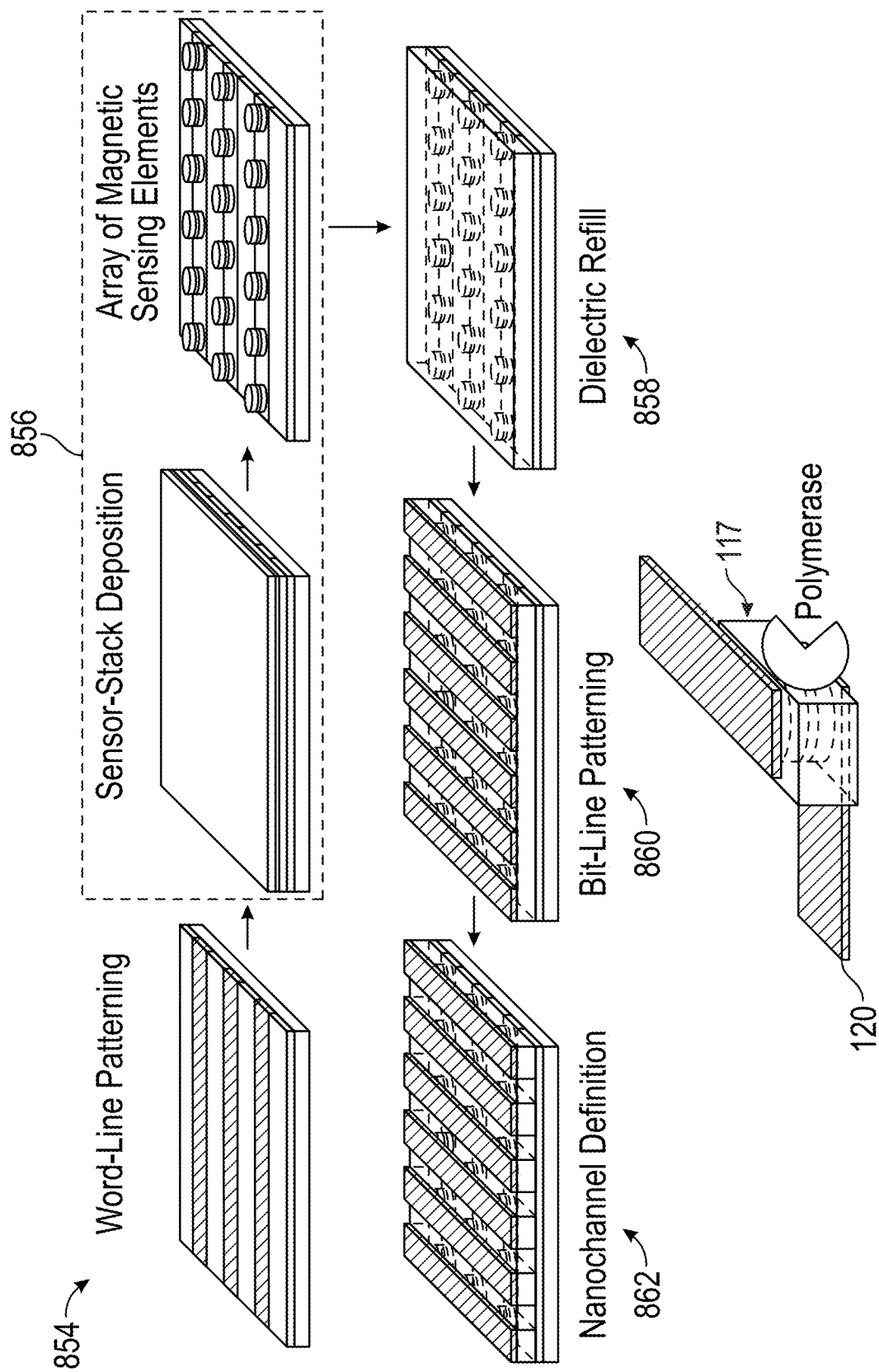
FIG. 14B illustrates the results of steps of the fabrication method of FIG. 14A in accordance with some embodiments.

In some embodiments, the detection device 100 is fabricated using photolithographic processes and thin film deposition. FIG. 14A illustrates a method 850 of manufacturing the detection device 100, and FIG. 14B illustrates the results of steps of the fabrication method 850 with a final panel showing polymerase bound to the wall 117 proximate to a sensor 105 in accordance with some embodiments (e.g., when the detection device 100 is used for nucleic acid sequencing). At 852, the method 850 begins. At 854, at least one line 120 is fabricated on a substrate, for example, by depositing one or more metal layers, using, for example, photolithography to pattern an array of lines and spaces in a polymer layer applied on top of the metal layers, using that polymer layer as a mask for etching the metal layers into an array of lines, depositing an insulating dielectric material, stripping the polymer layer and dielectric material over the lines, and performing chemical mechanical polishing to planarize the surface. At 856, the sensor array 110 is fabricated on the at least one line 120. Each sensor 105 of the sensor array 110 has a bottom portion 108 and a top portion 109. (See FIG. 1A.) The bottom portion 108 is coupled to the at least one line 120. In some embodiments, the bottom portion 108 of each sensor 105 is in contact with the at least one line 120.

At 858, dielectric material is deposited between the sensors 105 of the sensor array 110. At 860, additional lines 120 are fabricated. Each of these additional lines 120 is coupled to the top portion 109 of at least one sensor 105 in the sensor array 110. In some embodiments, the top portion 109 of each sensor 105 is in contact with a line 120. In some embodiments, the bottom portion 108 of a sensor 105 is in contact with a first line 120A, and the top portion 109 of the sensor 105 is in contact with a second line 120B. At 862, a portion of the dielectric material adjacent to the sensors 105 is removed (e.g., by milling, etching, or any other suitable removal process) to create the fluidic channel 115. At 864, the method 850 ends.

Electrical detection for DNA sequencing described in this disclosure may provide a variety of advantages over currently-used technologies involving optical detection methods. For example, electrical detection is not limited in terms of scaling flow cell dimensions in the same manner that optical detection is limited due to optical imaging being diffraction limited. Magnetic detection is a form of electrical detection for sequencing that has advantages over commonly proposed tunnel current detection schemes, because tunneling current methods measure very small currents (which reduces SNR), and the tunnel junction elements are exposed directly to the sequencing chemistries, which could cause corrosion or other detrimental issues that degrade the accuracy of the sequencing process. By comparison, magnetic detection has larger signals (and better SNR) and can be performed without labeling particles (e.g., MNPs) being in direct contact with the sensors 105, thereby allowing sensors 105 to be coated in a protective layer that mitigates interactions with the sequencing reagents.

For various embodiments described herein, the STO detection techniques can be used in a relatively simple binary process to detect the presence of an introduced DNA nucleotide precursor (e.g., via detection of a finite or approximately zero voltage at the output of an analog detection circuit). As such, it can reduce the SNR needed to operate the detection system at a high level of accuracy, which makes STO design easier. It also provides flexibility in the choice of MNPs used as labels for the molecules to be detected because only a small magnetic field without any particular field direction turns off or turns on the STO. Thus, both superparamagnetic and ferromagnetic particles may be used without use of an external magnetic field to align particles at different sites in the flow cell (e.g., sensor array 110).

Embodiments herein that use digital processing for detection may also be advantageous to detect changes in STO oscillation frequencies and/or frequency noise using reliable, accurate hardware components (e.g., filters, amplifiers, PLLs, DSPs, and/or other similar components) and well-understood algorithms (e.g., Fourier transforms or any other known frequency-analysis techniques to assess the frequency content and/or frequency noise of the RF signal).

A limitation of magnetic detection may be the SNR of the sensor 105. An advantage of some of the disclosed embodiments is that the STO 604 operates at a higher frequency and will thus have reduced $1/f$ noise, which results in reduced total noise in equilibrium conditions. Another advantage is that because a single voltage is detected at the output of the detector, use of STOs 604 should be fast and should allow for high data collection throughput, which is desirable in detection systems (e.g., for DNA sequencing).

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

The terms "over," "under," "between," "on", and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The terms "exemplary" and "embodiment" are used to express examples, not preferences or requirements. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrases "at least one of X, Y, and Z," "at least one of X, Y, or Z," "one or more of X, Y, and Z," and "one or more of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

The drawings are not necessarily to scale, and the dimensions, shapes, and sizes of the features may differ substantially from how they are depicted in the drawings.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes that come within the meaning and range of equivalency of the claims are to be embraced within their scope. Accordingly, the specification and drawings are to be regarded in an illustrative rather than a restrictive sense.

We claim:

1. A device for molecule detection, the device comprising:
   at least one fluidic channel configured to receive molecules to be detected, wherein at least some of the molecules to be detected are labeled by magnetic nanoparticles (MNPs);
   a sensor comprising a spin torque oscillator (STO) and encapsulated by a material separating the sensor from the at least one fluidic channel, wherein a surface of the material provides binding sites for the molecules to be detected; and
   detection circuitry coupled to the sensor and configured to detect a frequency or frequency noise of a radio-frequency (RF) signal generated by the STO in response to presence or absence of at least one MNP coupled to one or more binding sites associated with the sensor,
   wherein:
   the molecules to be detected include a first type of molecule and a second type of molecule, the first type of molecule being labeled by a first MNP type, and the second type of molecule being labeled by a second MNP type,
   the frequency or frequency noise of the RF signal generated by the STO is (a) a first frequency or frequency noise in response to presence of the first MNP type, or (b) a second frequency or frequency noise in response to presence of the second MNP type, and
   the detection circuitry is configured to distinguish between the first frequency or frequency noise and the second frequency or frequency noise to differentiate between the first and second types of molecules.

2. The device recited in claim 1, wherein the detection circuitry is configured to detect the frequency or the frequency noise of the RF signal generated by the STO in response to the presence or absence of the at least one MNP coupled to the one or more binding sites associated with the sensor by, in part, applying a DC current to the STO.

3. The device recited in claim 1, wherein the STO comprises a pinned layer, a free layer, and a spacer layer disposed between the pinned layer and the free layer.

4. The device recited in claim 3, wherein the pinned layer comprises one or more ferromagnetic (FM) layers.

5. The device recited in claim 4, wherein the one or more FM layers are first one or more FM layers, and wherein the free layer comprises second one or more FM layers.

6. The device recited in claim 5, wherein the spacer layer comprises an insulating layer or a metal layer.

7. The device recited in claim 3, wherein, in a quiescent state of magnetization, a magnetic moment of the free layer is oriented substantially co-linearly with a magnetic moment of the pinned layer.

8. The device recited in claim 3, wherein, in a quiescent state of magnetization, a magnetic moment of the free layer is oriented substantially parallel to or anti-parallel to a magnetic moment of the pinned layer.

9. The device recited in claim 3, wherein, in a quiescent state of magnetization, a magnetic moment of the free layer is oriented at an angle to a magnetic moment of the pinned layer, wherein the angle is between approximately 20 degrees and approximately 60 degrees.

10. A device for molecule detection, the device comprising:
    at least one fluidic channel configured to receive molecules to be detected, wherein at least some of the molecules to be detected are labeled by magnetic nanoparticles (MNPs);
    a sensor comprising a spin torque oscillator (STO) and encapsulated by a material separating the sensor from the at least one fluidic channel, wherein a surface of the material provides binding sites for the molecules to be detected; and
    detection circuitry coupled to the sensor and configured to detect a frequency or frequency noise of a radio-frequency (RF) signal generated by the STO in response to presence or absence of at least one MNP coupled to one or more binding sites associated with the sensor,
    wherein the detection circuitry comprises a delay line circuit comprising:
    a power divider configured to split the RF signal generated by the STO, or an amplified version of the RF signal generated by the STO, into a first signal routed to a first path having a first delay and a second signal routed to a second path having a second delay, wherein the second delay is greater than the first delay, a mixer having a first input coupled to the first path, a second input coupled to the second path, and an output, and a low pass or band pass filter coupled to the output of the mixer.

11. The device recited in claim 10, wherein the delay line circuit further comprises one or more of:

a first amplifier coupled to the power divider and disposed between the STO and the power divider to provide the amplified version of the RF signal generated by the STO to the power divider, or a second amplifier coupled to an output of the low pass or band pass filter.

12. The device recited in claim 10, wherein the first path comprises a first wire trace and the second path comprises a second wire trace, the second wire trace being longer than the first wire trace.

13. The device recited in claim 10, further comprising a phase shifter disposed on either the first or second path between the power divider and the mixer, wherein the phase shifter is configured to adjust a difference between a phase of the first signal and a phase of the second signal so that, in the absence of the at least one MNP coupled to one or more binding sites associated with the sensor, a DC output of the delay line circuit is below a threshold.

14. The device recited in claim 10, further comprising:
a spectrum analyzer coupled to an output of the low pass or band pass filter.

15. The device recited in claim 14, wherein the spectrum analyzer comprises non-transitory machine-executable instructions for execution by a processor.

16. A system, comprising:
the device recited in claim 10; and
a spectrum analyzer coupled to an output of the detection circuitry.

17. The device recited in claim 10, wherein the MNPs are superparamagnetic, and wherein the delay line circuit comprises a spectrum analyzer configured to detect the frequency noise of the RF signal generated by the STO based on a comparison of a measured integrated noise from the STO to a noise measurement from a reference STO not exposed to any MNP.

18. The device recited in claim 17, wherein the spectrum analyzer is implemented by a processor.

19. A device for molecule detection, the device comprising:
at least one fluidic channel configured to receive molecules to be detected, wherein at least some of the molecules to be detected are labeled by magnetic nanoparticles (MNPs);
a sensor comprising a spin torque oscillator (STO) and encapsulated by a material separating the sensor from the at least one fluidic channel, wherein a surface of the material provides binding sites for the molecules to be detected; and
detection circuitry coupled to the sensor and configured to detect a frequency or frequency noise of a radio-frequency (RF) signal generated by the STO in response to presence or absence of at least one MNP coupled to one or more binding sites associated with the sensor,
wherein the detection circuitry comprises a phase locked loop (PLL) configured to provide an error signal output that corresponds to the frequency noise of the RF signal generated by the STO in response to the presence of the at least one MNP coupled to the one or more binding sites associated with the sensor.

20. The device recited in claim 19, wherein the PLL comprises:
a loop filter; and
a low pass filter.

21. The device recited in claim 20, wherein the loop filter comprises an amplifier and at least one resistor.

22. The device recited in claim 20, wherein the detection circuitry further comprises:
a mixer having a first input, a second input, and an output; and
a reference oscillator with an input coupled to a tuning input from the PLL and an output coupled to the first input of the mixer,
wherein the STO is coupled to the second input of the mixer, and the output of the mixer is coupled to an input of the low pass filter.

23. A method of sequencing nucleic acid using a device, the device comprising a plurality of spin torque oscillators (STOs) and at least one fluidic channel, the method comprising:
labeling a nucleotide precursor with a magnetic nanoparticle (MNP);
adding the labeled nucleotide precursor to the at least one fluidic channel of the device;
detecting a frequency or frequency noise of a radio-frequency (RF) signal generated by at least one of the plurality of STOs;
based at least in part on the detected frequency or frequency noise of the RF signal generated by the at least one of the plurality of STOs, determining whether the labeled nucleotide precursor has been detected; and
in response to determining that the labeled nucleotide precursor has been detected, recording (a) an identity of the nucleotide precursor, or (b) an identity of a base complementary to the labeled nucleotide precursor.

24. The method of claim 23, wherein detecting the frequency or frequency noise of the RF signal generated by at least one of the plurality of STOs comprises:
detecting an amplitude of a DC signal at an output of a delay line circuit coupled to the at least one of the plurality of STOs.

25. The method of claim 23, wherein detecting the frequency or frequency noise of the RF signal generated by at least one of the plurality of STOs comprises:
monitoring an error signal of a detection circuit comprising a phase locked loop.

26. The method of claim 23, wherein the MNP is superparamagnetic, and wherein detecting the frequency or frequency noise of the RF signal generated by at least one of the plurality of STOs comprises:
determining a spectral density of the RF signal generated by the at least one of the plurality of STOs,
integrating the spectral density, and
comparing the integrated spectral density to a reference noise associated with a reference STO, the reference STO not being influenced by any MNP.

27. The method of claim 23, further comprising:
before adding the labeled nucleotide precursor to the fluidic channel of the device, binding at least one nucleic acid strand to a binding site in the fluidic channel, and adding, to the fluidic channel, an extendable primer and a plurality of molecules of nucleic acid polymerase.

28. A method of sequencing nucleic acid using a device, the device comprising a plurality of spin torque oscillators (STOs) and at least one fluidic channel, the method comprising:

labeling a first nucleotide precursor with a first magnetic nanoparticle (MNP) type, the first MNP type selected to cause a magnetization of each of the plurality of STOs to oscillate at a first frequency;

labeling a second nucleotide precursor with a second MNP type, the second MNP type selected to cause the magnetization of each of the plurality of STOs to oscillate at a second frequency;

adding the labeled first and second nucleotide precursors to the fluidic channel of the device;

using a delay line circuit, detecting a frequency of a signal generated by at least one of the plurality of STOs; and in response to the detected frequency, identifying whether the first nucleotide precursor or the second nucleotide precursor has been detected.

29. The method of claim 28, wherein detecting the frequency of the signal generated by the at least one of the plurality of STOs comprises:

splitting a signal originating from the at least one of the plurality of STOs into a first signal and a second signal;

routing the first signal to a mixer via a first path having a first delay;

routing the second signal to the mixer via a second path having a second delay, the second delay being longer than the first delay;

the mixer mixing the delayed first and second signals; and a low pass filter filtering an output from the mixer, and wherein identifying whether the first nucleotide precursor or the second nucleotide precursor has been detected comprises:

analyzing an output of the low pass filter or an amplified version of the output of the low pass filter.

30. The method of claim 29, wherein detecting the frequency of the signal generated by the at least one of the plurality of STOs further comprises:

shifting a phase of the first signal or the second signal.

31. The method of claim 29, wherein detecting the frequency of the signal generated by the at least one of the plurality of STOs further comprises:

amplifying the output of the low pass filter.

32. The method of claim 29, wherein analyzing the output of the low pass filter or the amplified version of the output of the low pass filter comprises:

accessing a look-up table to determine whether the output of the low pass filter or the amplified version of the output of the low pass filter corresponds to a first expected value for the first nucleotide precursor or a second expected value for the second nucleotide precursor; or determining whether the output of the low pass filter or the amplified version of the output of the low pass filter is in a first range associated with the first nucleotide precursor or a second range associated with the second nucleotide precursor.

33. A system for sequencing nucleic acid, the system comprising:

a plurality of spin torque oscillators (STOs);

a fluidic channel;

means for labeling a nucleotide precursor with a magnetic nanoparticle (MNP);

means for adding the labeled nucleotide precursor to the fluidic channel;

means for detecting a frequency or frequency noise of a radio-frequency (RF) signal generated by at least one of the plurality of STOs;

means for determining, based at least in part on the detected frequency or frequency noise of the RF signal generated by the at least one of the plurality of STOs, whether the labeled nucleotide precursor has been detected; and means for recording (a) an identity of the nucleotide precursor, (b) an identity of a base complementary to the labeled nucleotide precursor, or (c) both (a) and (b).

34. The system of claim 33, further comprising:

means for binding at least one nucleic acid strand to a binding site in the fluidic channel; and means for adding, to the fluidic channel, an extendable primer and a plurality of molecules of nucleic acid polymerase.

* * * * *